(12) United States Patent
Pan et al.

(10) Patent No.: US 9,284,537 B2
(45) Date of Patent: Mar. 15, 2016

(54) **CYTOCHROME P450 ENZYMES FROM *SORGHUM BICOLOR***

(71) Applicant: The United States of America, as Represented by the Secretary of Agriculture, Washington, DC (US)

(72) Inventors: Zhiqiang Pan, Oxford, MS (US); Scott R. Baerson, Oxford, MS (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 281 days.

(21) Appl. No.: 13/862,883

(22) Filed: Apr. 15, 2013

(65) Prior Publication Data

US 2014/0308731 A1 Oct. 16, 2014

(51) Int. Cl.
*C12N 9/02* (2006.01)
*C12P 7/22* (2006.01)
*C12P 7/66* (2006.01)

(52) U.S. Cl.
CPC ............ *C12N 9/0071* (2013.01); *C12N 9/0073* (2013.01); *C12P 7/22* (2013.01); *C12P 7/66* (2013.01); *C12Y 114/13* (2013.01)

(58) Field of Classification Search
None
See application file for complete search history.

(56) References Cited

U.S. PATENT DOCUMENTS

| | | | |
|---|---|---|---|
| 7,732,666 B1 | 6/2010 | Baerson et al. | |
| 8,383,890 B1 | 2/2013 | Pan et al. | |
| 2011/0225676 A1* | 9/2011 | Baerson et al. | 800/281 |

OTHER PUBLICATIONS

Cook et al., 2010, The Plant Cell 22: 867-887.*
Baerson et al., 2008, J. Biol. Chem. 283: 3231-3247.*
Paterson et al., 2009, Nature 547: 551-556.*
GenBank sequence Accession No. XM_002451987.1, published Jul. 13, 2009.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Chang, M. et al., Chemical Regulation of Distance : Characterization of the First Natural Host Germination Stimulant for Striga asiatica, J. Am. Chem. Soc., 1986, pp. 7858-7860, vol. 108.
Cho, H.-T. et al., Regulation of Root Hair Initiation and Expansin Gene Expression in Arabidopsis, The Plant Cell., 2002, pp. 3237-3253, vol. 14.
Czarnota, M.A. et al., Evaluation of Root Exudates of Seven Sorghum Accessions, Journal of Chemical Ecology, 2003, pp. 2073-2083, vol. 29 (9).
Czarnota, M.A. et al., Anatomy of Sorgoleone-Secreting Root Hairs of *Sorghum* Species, Int. J. Plant Sci., 2003, pp. 861-866, vol. 164 (6).
Czarnota, M.A. et al., Mode of Action, Localization of Production, Chemical Nature, and Activity of Sorgoleone: A Potent PSII Inhibitor in *Sorghum* spp. Root Exudates, Weed Technology, 2001, pp. 813-825, vol. 15.
Duke, S.O. et al., Weeding with Transgenes, Trends in Biotechnology, 2003, pp. 192-195, vol. 21 (5).
Einhellig, F.A., Interactions Involving Allelopathy in Cropping Systems, Agron. J., 1996, pp. 886-893, vol. 88.
Einhellig, F.A., et al., Phytotoxicity of Sorgoleone Found in Grain Sorghum Root Exudates, Journal of Chemical Ecology, 1992, pp. 1-11, vol. 18 (1).
Kagan, I.A. et al., Chomatographic Separation and in Vitro Activity of Sorgoleone Congeners from the Roots of Sorghum Bicolor, Journal of Agricultural and Food Chemistry, 2003, pp. 7589-7595, vol. 51.
Kim, C.M. et al., OsCSLD1, a Cellulose Synthase-Like D1 Gene, is Required for Root Hair Morphogenesis in Rice, Plant Physiology, 2007, pp. 1220-1230, vol. 143.
Netzly, D.H. et al., Roots of Sorghum Exude Hydrophobic Droplets Containing Biologically Active Components, Crop Science, 1986, pp. 775-778, vol. 26.
Nimbal, C.I. et al., Phytotoxicity and Distribution of Sorgoleone in Grain Sorghum Germplasm, J. Agric. Food Chem., 1996, pp. 1343-1347, vol. 44.
Pan, Z. et al., Functional Characterization of Desatruases Involved in the Formation o the Terminal Double Bond of an Unusual 16:3 Fatty Acid Isolated from Sorghum bicolor Root Hairs, The Journal of Biological Chemistry, 2007, pp. 4326-4335, vol. 282 (7).
Rimando, A.M. et al., PSII Inhibitory Activity of Resorcinolic Lipids from Sorghum bicolor, J. Nat. Prod., 2003, pp. 42-45, vol. 66.
Yu, Z. et al., Root Hair-Specific Expansins Modulate Root Hair Elongation in Rice, The Plant Journal, 2011, pp. 725-734, vol. 66.

* cited by examiner

*Primary Examiner* — David T Fox
*Assistant Examiner* — Bratislav Stankovic
(74) *Attorney, Agent, or Firm* — John D. Fado; David L. Marks; Lesley Shaw

(57) ABSTRACT

Two novel cytochrome P450 genes are isolated from sorghum, each gene encoding a protein having pentadecatrienyl resorcinol hydroxylase activity. Expression vectors containing these sequences are made and used to elevate levels of pentadecatrienyl resorcinol hydroxylase in transgenic cells and organisms.

17 Claims, 4 Drawing Sheets

CYTOCHROME P450 ENZYMES FROM *SORGHUM BICOLOR*

BACKGROUND OF THE INVENTION

1. Field of the Invention

This invention relates to two novel pentadecatrienyl resorcinol hydroxylases which are in the cytochrome P450 gene superfamily. This invention relates to the DNA sequences of these novel enzymes, the amino acid sequences of these novel enzymes, expression vectors containing the DNA sequences of these novel enzymes, methods of making these novel enzymes, methods of transforming plants to express these novel enzymes, and transgenic plants expressing these novel enzymes which may result in the production of dihydrosorgoleone which may be secreted by a plant and undergo oxidation to become sorgoleone.

2. Prior Art Description

Allelopathy, sometimes referred to as a form of chemical warfare between plants, can be defined as the production and release of chemical substances by one species that inhibit the growth of another species (Inderjit and Duke, *Planta* 217: 529-539 (2003); Weston and Duke, *Crit. Rev. Plant Sci.* 22:367-389 (2003)). Allelopathic interactions have been proposed to have profound effects on the evolution of plant communities through the loss of susceptible species via chemical interference, and by imposing selective pressure favoring individuals resistant to inhibition from a given allelochemical (e.g., Schulz and Wieland, *Chemoecology* 9:133-141 (1999)). Furthermore, allelopathic compounds released by grain crop species are thought to play a significant role in cover crops or within intercropping systems where they act as weed suppressants. Allelopathic compounds have been characterized in a number of plants such as black walnut, wheat, rice, and sorghum (Bertin, et al., *Plant and Soil* 256: 67-83 (2003); Inderjit and Duke, (2003); Duke et al., *Outlooks Pest Management* 16: 64-68 (2005)). These chemicals which can be produced and released by many types of plants, algae, bacteria, and fungi and which often involve secondary metabolites, are referred to as allelochemicals or phytotoxins when produced by plants. Of note, allelopathy and allelochemicals can also positively influence the growth, survival, and reproduction of other organisms.

Despite the ecological and agronomic importance of allelochemicals, relatively few pathways have been characterized in detail at the molecular level. One notable exception is the identification and characterization of all the genes encoding the enzymes responsible for the biosynthesis of 2,4-dihydroxy-7-methoxy-2H-1,4-benzoxazin-3(4H)-one, a benzoxazinoid, in *Zea mays* (Frey et al., *Science* 277:696-699 (1997)). Benzoxazinoids are thought to act as alleopathic chemicals in the rhizosphere, in addition to being defense compounds against microbial pathogens and insect herbivores (Sicker et al., *Int. Rev. Cytol.* 198:319-346 (2000); Friebe, *J. Crop Prod.* 4:379-400 (2001)).

Several *Sorghum* species have been reported to produce phytotoxins (secondary metabolites) which are exuded from their root systems into the rhizosphere, which suppress the growth of competing species (Einhellig, *Agronomy Journal* 88:886-893 (1996)). Numerous studies have contributed to the discovery and identification of the chemicals that are responsible for this observed allelopathic inhibition. For example, studies on the biologically-active components of both water-soluble and water-insoluble exudates from roots of *Sorghum bicolor* have demonstrated their role in the growth inhibition of lettuce seedlings (*Lactuca sativa*), as well as a number of important invasive weed species (Netzly and Butler, *Crop Science* 26:775-778 (1986)). The major constituent of these exudates was identified as 2-hydroxy-5-methoxy-3-[(Z,Z)-8',11',14'-pentadecatriene]-p-benzoquinone, referred to as sorgoleone (Chang, et al., *J. Am. Chem. Soc.* 108:7858-7860 (1986)), which has been estimated to account for as much as 85% of the exudate material (w/w) in some varieties of sorghum (Czarnota, et al., *Weed Technology* 15:815-825 (2001)). The remaining exudate consists largely of sorgoleone congeners differing in the length or degree of saturation of the aliphatic side chain, and in the substitution pattern of the quinone ring (Kagan, et al., *J. Agric. Food Chem.* 51:7589-7595 (2003); Rimando, et al., *J. Nat. Prod.* 66:42-45 (2003)). Sorgoleone acts as a potent broad-spectrum inhibitor active against many agronomically important monocot and dicot weed species, exhibits a long half-life in soil, and appears to affect multiple targets in vivo (e.g., Netzly and Butler, 1986; Einhellig and Souza, *J. Chemical Ecology* 18:1-11 (1992); Nimbal, et al., *J. Agric. Food Chem.* 44:1343-1347 (1996); Czarnota, et al., 2001; Bertin, et al., 2003; Duke, *Trends Biotechnol.* 21:192-195 (2003)). Sorgoleone is a promising natural product alternative to synthetic herbicides (Duke, 2003).

The herbicidal and allelopathic properties of sorgoleone make the isolation and characterization of the corresponding genes involved in sorgoleone biosynthesis highly desirable, as manipulation of the pathway in sorghum, or genetic modification of other plant species using these genes could provide important insights into the underlying allelochemical interactions involved (Duke, 2003). Sorgoleone biosynthesis is likely restricted to root hairs, which appear as cytoplasmically dense cells in sorghum, containing large osmiophilic globules deposited between the plasmalemma and cell wall, presumably associated with sorgoleone rhizosecretion (Czarnota, et al., *Int. J. Plant Sci.* 164:861-866 (2003b); Czarnota, et al., *J. Chem. Ecology* 29:2073-2083 (2003a)). The biosynthetic pathway of sorgoleone appears to require four types of enzymes: fatty acid desaturases, polyketide synthases, O-methyltransferases, and cytochrome P450 monooxygenases (FIG. 1). Recently, the following enzymes in this pathway have been characterized: two *S. bicolor* fatty acid desaturases (DES2, DES3; Pan, et al., *J. Biol. Chem.* 282:4326-4335 (2007) and U.S. Pat. No. 8,383,890), two alkylresorcinol synthases (ARS1, ARS2; U.S. Patent Pub. 2011-0225676), and a 5-n-alk(en)ylresorcinol-utilizing O-methyltransferase (OMT3; U.S. Pat. No. 7,732,666) which likely participate in the biosynthesis of sorgoleone. As of yet, the enzyme or enzymes that convert 3-methyl-5-pentadecatrienyl resorcinol to dihydrosorgoleone, a vital step in the biosynthesis of sorgoleone, have not been isolated or characterized.

BRIEF DESCRIPTION OF THE INVENTION

It is an object of this invention to have two novel pentadecatrienyl resorcinol hydroxylases with distinct DNA sequences.

It is an object of this invention to have an isolated polynucleotide encoding each novel pentadecatrienyl resorcinol hydroxylase. It is a further object of this invention that the amino acid sequence of pentadecatrienyl resorcinol hydroxylase is SEQ ID NO: 12 and SEQ ID NO: 14. It is another object of this invention to have an isolated polynucleotide encoding a polypeptide that is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to each novel pentadecatrienyl resorcinol hydroxylase.

It is an object of this invention to have an isolated polynucleotide encoding one of the novel pentadecatrienyl resorcinol hydroxylases or a polypeptide that is at least 95%, at least 90% or at least 85% identical to the amino acid sequence of one of the novel pentadecatrienyl resorcinol hydroxylases. It is a further object of this invention to have a promoter operatively linked to the polynucleotide encoding one of the novel pentadecatrienyl resorcinol hydroxylases or encoding a polypeptide that is at least 95%, at least 90% or at least 85% identical to the amino acid sequence of one of the novel pentadecatrienyl resorcinol hydroxylases. It is another object on this invention that the promoter is active in one or more of the following: plants, fungi, blue-green algae, bacteria, and animals.

It is an object of this invention to have an isolated polynucleotide encoding one of the novel pentadecatrienyl resorcinol hydroxylases or a polypeptide that is at least 95%, at least 90% or at least 85% identical to the amino acid sequence of one of the novel pentadecatrienyl resorcinol hydroxylases. It is a further object of this invention to have a promoter operatively linked to the polynucleotide encoding one of the novel pentadecatrienyl resorcinol hydroxylases or encoding a polypeptide that is at least 95%, at least 90% or at least 85% identical to the amino acid sequence of one of the novel pentadecatrienyl resorcinol hydroxylases. It is another object on this invention that the promoter is active in one or more of the following: plants, fungi, blue-green algae, bacteria, and animals. It is a further object of this invention that the promoter be either an inducible promoter or a constitutive promoter. It is another object of this invention that the promoter be a tissue-specific promoter.

It is an object of this invention to have an isolated polynucleotide encoding each novel pentadecatrienyl resorcinol hydroxylase or a polypeptide that is at least 95%, at least 90% or at least 85% identical to the amino acid sequence of each novel pentadecatrienyl resorcinol hydroxylase. It is a further object of this invention to have a promoter operatively linked to the polynucleotide encoding each novel pentadecatrienyl resorcinol hydroxylase or encoding a polypeptide that is at least 95%, at least 90% or at least 85% identical to the amino acid sequence of each novel pentadecatrienyl resorcinol hydroxylase. It is another object on this invention that the promoter is active in plants, and more specifically in the root cells of a plant, and more specifically in the root hair cells of a plant.

It is an object of this invention to have an expression vector containing a promoter operatively linked to a polynucleotide encoding one of the following: one of the novel pentadecatrienyl resorcinol hydroxylases, or a polypeptide that is at least 95%, at least 90% or at least 85% identical to the amino acid sequence of one of the novel pentadecatrienyl resorcinol hydroxylases. It is another object on this invention that the promoter is active in one or more of the following: plants, fungi, blue-green algae, bacteria, and animals. It is a further object of this invention that the promoter be either an inducible promoter or a constitutive promoter. It is another object of this invention that the promoter be a tissue-specific promoter.

It is an object of this invention to have a transformed cell which is transformed with an expression vector containing a promoter operatively linked to a polynucleotide encoding one of the following: one of the novel pentadecatrienyl resorcinol hydroxylases, or a polypeptide that is at least 95%, at least 90% or at least 85% identical to the amino acid sequence of one of the novel pentadecatrienyl resorcinol hydroxylases. It is another object of this invention that the promoter is active in one or more of the following: plants, fungi, blue-green algae, bacteria, and animals. It is a further object of this invention that the promoter be either an inducible promoter or a constitutive promoter. It is another object of this invention that the promoter be a tissue-specific promoter.

It is an object of this invention to have a transformed cell which is transformed with an expression vector containing a promoter operatively linked to a polynucleotide encoding one of the following: one of the novel pentadecatrienyl resorcinol hydroxylases, or a polypeptide that is at least 95%, at least 90% or at least 85% identical to the amino acid sequence of one of the novel pentadecatrienyl resorcinol hydroxylases. It is another object of this invention that the promoter is active in one or more of the following: plants, fungi, blue-green algae, bacteria, and animals. It is a further object of this invention that the promoter be either an inducible promoter or a constitutive promoter or tissue-specific promoter. It is a further object of this invention that the transformed cell be a plant cell, a fungus, a blue-green algae, or a bacterium.

It is an object of this invention to have a transformed cell which is transformed with an expression vector containing a promoter operatively linked to a polynucleotide encoding one of the following: one of the novel pentadecatrienyl resorcinol hydroxylases, or a polypeptide that is at least 95%, at least 90% or at least 85% identical to the amino acid sequence of one of the novel pentadecatrienyl resorcinol hydroxylases. It is another object of this invention that the promoter is active in plants, and more specifically in the root cells of a plant, and more specifically in the root hair cells of a plant. It is another object of this invention that the transformed cell be a plant cell.

It is an object of this invention to have a transformed organism contains a polynucleotide encoding one of the novel pentadecatrienyl resorcinol hydroxylase or a polypeptide that is at least 95%, at least 90% or at least 85% identical to the amino acid sequence of one of the novel pentadecatrienyl resorcinol hydroxylases. It is another object of this invention that the transformed organism has elevated levels of pentadecatrienyl resorcinol hydroxylase compared to a wild-type organism. It is another object of this invention that the organism can be a plant, fungi, blue-green algae, or bacteria. It is further object of this invention that the polynucleotide be operably linked to a promoter that is active in the organism. It is another object of this invention that the promoter be an inducible promoter, a constitutive promoter, or a tissue-specific promoter.

It is an object of this invention to have an isolated polynucleotide encoding each novel pentadecatrienyl resorcinol hydroxylase. It is a further object of this invention that the DNA sequence of pentadecatrienyl resorcinol hydroxylase is SEQ ID NO: 11 and SEQ ID NO: 13. It is another object of this invention to have an isolated polynucleotide having a sequence that is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the DNA sequence of each novel pentadecatrienyl resorcinol hydroxylase.

It is an object of this invention to have an isolated polynucleotide for one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is a further object of this invention to have a promoter operatively linked to the polynucleotide for one of the novel pentadecatrienyl resorcinol hydroxylases or a DNA sequence that is at least 95%, at least 90% or at least 85% identical to the DNA sequence of one of the novel pentadecatrienyl resorcinol hydroxylase genes. It is another object on this invention that the promoter is active in one or more of the following: plants, fungi, blue-green algae, bacteria, and animals.

It is an object of this invention to have an isolated polynucleotide for one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is a further object of this invention to have a promoter operatively linked to the polynucleotide for one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is another object on this invention that the promoter is active in one or more of the following: plants, fungi, blue-green algae, bacteria, and animals. It is a further object of this invention that the promoter be an inducible promoter, a constitutive promoter, or a tissue-specific promoter.

It is an object of this invention to have an isolated polynucleotide for one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is a further object of this invention to have a promoter operatively linked to the polynucleotide for one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is another object on this invention that the promoter is active in plants, and more specifically in the root cells of a plant, and more specifically in the root hair cells of a plant.

It is an object of this invention to have an expression vector containing a promoter operatively linked to a polynucleotide having one of the following DNA sequences: one of the novel pentadecatrienyl resorcinol hydroxylase genes, or a DNA sequence that is at least 95%, at least 90% or at least 85% identical to the DNA sequence of one of the novel pentadecatrienyl resorcinol hydroxylase genes. It is another object on this invention that the promoter is active in one or more of the following: plants, fungi, blue-green algae, bacteria, and animals. It is a further object of this invention that the promoter be an inducible promoter, a constitutive promoter, or a tissue specific promoter.

It is an object of this invention to have transformed cell which is transformed with an expression vector containing a promoter operatively linked to a polynucleotide having one of the following DNA sequences: one of the novel pentadecatrienyl resorcinol hydroxylase genes, or a DNA sequence that is at least 95%, at least 90% or at least 85% identical to the DNA sequence of one of the novel pentadecatrienyl resorcinol hydroxylase genes. It is another object on this invention that the promoter is active in one or more of the following: plants, fungi, blue-green algae, bacteria, and animals. It is a further object of this invention that the promoter be an inducible promoter, a constitutive promoter, or a tissue-specific promoter.

It is an object of this invention to have transformed cell which is transformed with an expression vector containing a promoter operatively linked to a polynucleotide having one of the following DNA sequences: one of the novel pentadecatrienyl resorcinol hydroxylase genes, or a DNA sequence that is at least 95%, at least 90% or at least 85% identical to the DNA sequence of one of the novel pentadecatrienyl resorcinol hydroxylase genes. It is another object on this invention that the promoter is active in one or more of the following: plants, fungi, blue-green algae, bacteria, and animals. It is a further object of this invention that the promoter be an inducible promoter, a constitutive promoter, or a tissue-specific promoter. It is a further object of this invention that the transformed cell be a plant cell, a fungus, a blue-green algae, or a bacterium.

It is an object of this invention to have transformed cell which is transformed with an expression vector containing a promoter operatively linked to a polynucleotide having one of the following DNA sequences: one of the novel pentadecatrienyl resorcinol hydroxylase genes, or a DNA sequence that is at least 95%, at least 90% or at least 85% identical to the DNA sequence of one of the novel pentadecatrienyl resorcinol hydroxylase genes. It is another object on this invention that the promoter is active in plants, and more specifically in the root cells of a plant, and more specifically in the root hair cells of a plant. It is another object of this invention that the transformed cell be a plant cell.

It is an object of this invention to have a transformed organism contains a polynucleotide having a DNA sequence of one of the novel pentadecatrienyl resorcinol hydroxylase genes or a DNA sequence that is at least 95%, at least 90% or at least 85% identical to the DNA sequence of one of the novel pentadecatrienyl resorcinol hydroxylase genes. It is another object of this invention that the transformed organism has elevated levels of pentadecatrienyl resorcinol hydroxylase compared to a wild-type organism. It is another object of this invention that the organism can be a plant, fungi, blue-green algae, or bacteria. It is further object of this invention that the polynucleotide be operably linked to a promoter that is active in the organism.

It is an object of this invention to have a method to produce dihydrosorgoleone in a plant or a plant cell. It is a further object of this invention to have a method of producing dihydrosorgoleone in a plant or a plant cell by transforming the plant or plant cell with polynucleotides encoding two fatty acid desaturases, an alkylresorcinol synthase, an O-methyltransferase, and a pentadecatrienyl resorcinol hydroxylase and allowing the polynucleotides to be expressed in the plant or plant cell. It is another object of this invention that the polynucleotides are contained in one or more expression vectors. It is still another object of this invention that each of the polynucleotides are operably linked to a promoter and further that the promoter is active in the plant or plant cell.

It is an object of this invention to have a method to produce dihydrosorgoleone in a plant or a plant cell. It is a further object of this invention to have a method of producing dihydrosorgoleone in a plant or a plant cell by transforming the plant or plant cell with polynucleotides encoding two fatty acid desaturases, an alkylresorcinol synthase, an O-methyltransferase, and a pentadecatrienyl resorcinol hydroxylase and allowing the polynucleotides to be expressed in the plant or plant cell. It is another object of this invention that the polynucleotides are contained in one or more expression vectors. It is still another object of this invention that each of the polynucleotides are operably linked to a promoter and further that the promoter is active in the plant or plant cell. It is a further object of this invention that the two fatty acid desaturases are SbDES2 and SbDES3, the alkylresorcinol synthase is either SbARS1 or SbARS2, the O-methyltransferase is SbOMT3, and the pentadecatrienyl resorcinol hydroxylase is either SbPRH1 or SbPRH2.

It is another object of this invention to have a transformed cell having elevated levels of pentadecatrienyl resorcinol hydroxylase compared to untransformed cells. It is a further object of this invention that the transformed cells contain an expression vector which encodes pentadecatrienyl resorcinol hydroxylase.

It is an object of this invention to have an isolated polypeptide which has one of the following amino acid sequences: the amino acid sequence of SEQ ID NO: 12; an amino acid sequence that is at least 99%, at least 98%, at least 97%, at least 96%, at least 95%, at least 94%, at least 93%, at least 92%, at least 91%, at least 90%, at least 89%, at least 88%, at least 87%, at least 86%, or at least 85% identical to the amino acid sequence of SEQ ID NO: 12; the amino acid sequence of SEQ ID NO: 14; or an amino acid sequence that is at least 99%, at least 98%, at least 97%, at least 96%, at least 95%, at least 94%, at least 93%, at least 92%, at least 91%, at least 90%, at least 89%, at least 88%, at least 87%, at least 86%, or at least 85% identical to the amino acid sequence of SEQ ID NO: 14.

It is another object of this invention to have a method of manipulating pentadecatrienyl resorcinol hydroxylase levels in a cell or organism. It is another object of this invention to have a method of manipulating pentadecatrienyl resorcinol hydroxylase levels in a cell or organism by introducing into the cell or organism an expression vector containing a polynucleotide operably linked to a promoter and allowing the production of pentadecatrienyl resorcinol hydroxylase in the cell or organism. It is a further object of this invention that the polynucleotide encodes a polypeptide having one of the following amino acid sequences: the amino acid sequence of SEQ ID NO: 12; an amino acid sequence that is at least 99%, at least 98%, at least 97%, at least 96%, at least 95%, at least 94%, at least 93%, at least 92%, at least 91%, at least 90%, at least 89%, at least 88%, at least 87%, at least 86%, or at least 85% identical to the amino acid sequence of SEQ ID NO: 12; the amino acid sequence of SEQ ID NO: 14; or an amino acid sequence that is at least 99%, at least 98%, at least 97%, at least 96%, at least 95%, at least 94%, at least 93%, at least 92%, at least 91%, at least 90%, at least 89%, at least 88%, at least 87%, at least 86%, or at least 85% identical to the amino acid sequence of SEQ ID NO: 14. It is yet a further object of this invention that the promoter is active in the cell or organism. It is another object of this invention that the promoter is an inducible promoter, a constitutive promoter, or a tissue-specific promoter.

BRIEF DESCRIPTION OF THE FIGURES

FIG. 4A is the mass spectrum for sorgoleone extracted from sorghum roots. FIGS. 4B and 4C are the mass spectra for extracts from yeast cells expressing CYP71AM1 and CYP71V7, respectively, exogenously provided with 3-methyl-5-pentadecatrienyl resorcinol via the culture media.

DETAILED DESCRIPTION OF THE INVENTION

Figure 1:
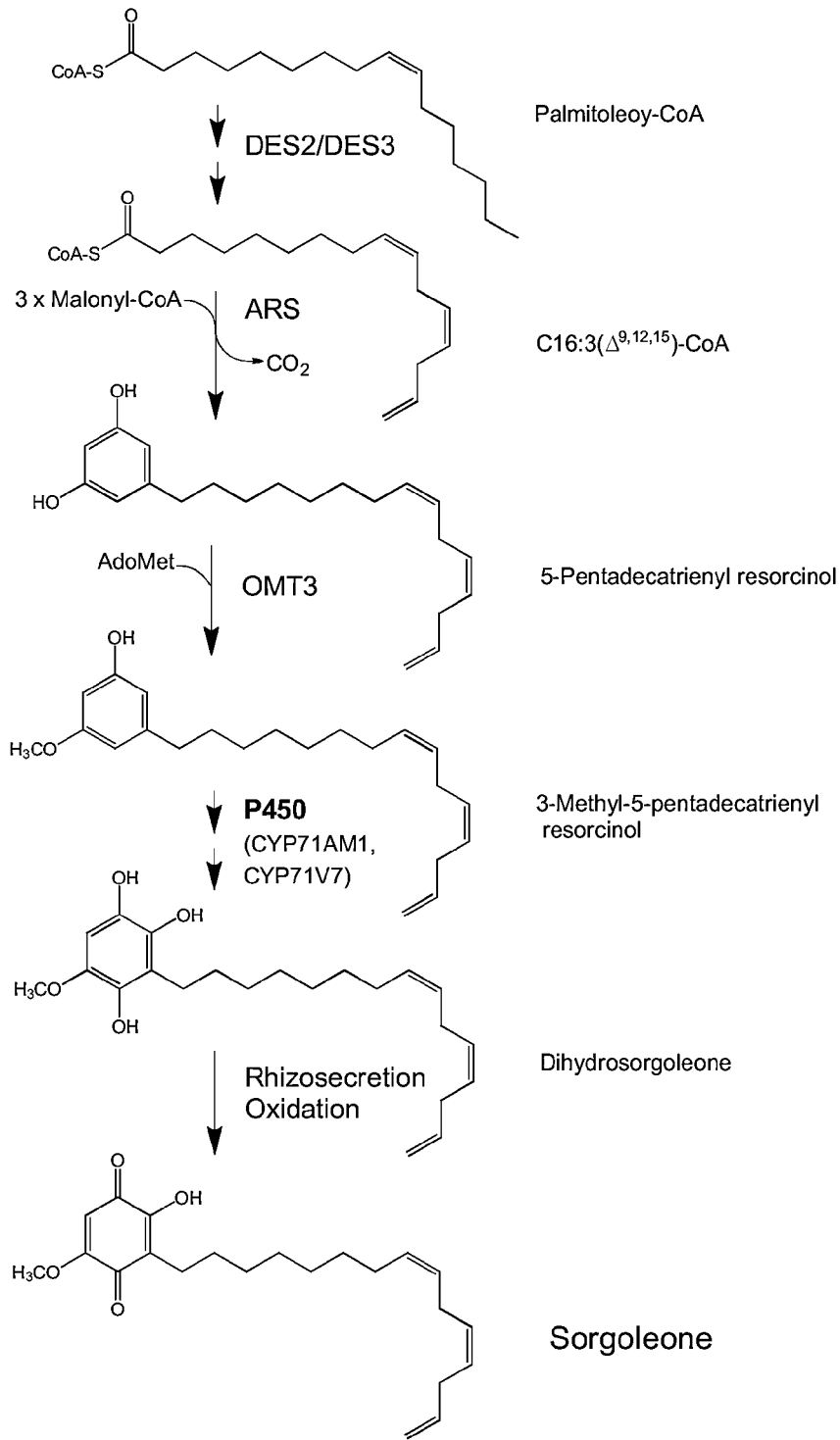
FIG. 1 shows the proposed biosynthetic pathway of sorgoleone.

This invention involves the isolation, sequencing, and functional characterization of two cytochrome P450 monooxygenases, designated CYP71V7 and CYP71AM1, which convert 5-pentadecatrienyl resorcinol-3-methyl ester to dihydrosorgoleone, a reduced form of sorgoleone, which, upon rhizosecretion, rapidly undergoes oxidation to the benzoquinone sorgoleone (see, Cook, et al., *Plant Cell* 22:867-887 (2010); Dayan, et al., *Phytochemistry* 71:1032-1039 (2010); FIG. 1). The isolation, sequencing, and characterization of CYP71AM1 and CYP71V7 from sorghum provides new genetic engineering opportunities in plants, not only for altering sorgoleone content leading to the generation of novel germplasm possessing enhanced agronomic characteristics, but also for the use of plants cells as bioreactors, thus providing an efficient source for obtaining sorgoleone and related phenolic lipids in large-scale. In addition to plants transformed with CYP71V7 and/or CYP71AM1 and producing the gene product(s), one can transform fungi or green algae with one or both of these genes. Then the transformed fungi or transformed green algae can produce the gene product(s) and convert 5-pentadecatrienyl resorcinol-3-methyl ester to dihydrosorgoleone. Also the transformed fungi or green algae can generate certain phenolic lipids by producing one or both of these genes and providing specific substrates to the transformed green algae and/or fungi.

The terms "isolated", "purified", or "biologically pure" as used herein, refer to material that is substantially or essentially free from components that normally accompany the material in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyino sine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. Probes may contain a label so that one can determine if the probe is bound to the target sequence. By assaying for the presence or absence of the probe, one can detect the presence or absence of the select sequence or subsequence.

The term "label" as used herein, refers to a composition detectable by spectroscopic, photochemical, biochemical, immunochemical, or chemical means. A probe can be bound, either covalently, through a linker or a chemical bond, or noncovalently, through ionic, van der Waals, electrostatic, or hydrogen bonds, to a label such that the presence of the probe may be detected by detecting the presence of the label bound to the probe. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available. In one exemplary embodiment, labels can be isotopes, chromophores, lumiphores, chromogens, etc. Labels can also involve two or more compounds, only one of which need be attached to the probe. An example of a pair of compounds that are labels is biotin and streptavidin, where biotin is attached to the probe and later reacts with streptavidin which is added after the probe binds the target sequence. In this embodiments, the probes are indirectly labeled, because the label (streptavidin) later binds to the biotin which is attached to the probe.

The term "primer" as used herein, refers to short nucleic acids, typically a DNA oligonucleotide of at least about 15 nucleotides in length. In an exemplary embodiment, primers are annealed to a complementary target DNA or RNA strand by nucleic acid hybridization to form a hybrid between the primer and the target DNA or RNA strand. Annealed primers are then extended along the target strand by a DNA polymerase enzyme or reverse transcriptase. Primer pairs can be used for amplification of a nucleic acid sequence, e.g., by the polymerase chain reaction (PCR) or other nucleic-acid amplification methods known in the art. PCR primer pairs are typically derived from a known sequence, for example, by using computer programs intended for that purpose such as Primer (Version 0.5 ©1991, Whitehead Institute for Biomedical Research, Cambridge, Mass.).

One of ordinary skill in the art will appreciate that the specificity of a particular probe or primer increases with its length. Thus, for example, a primer or probe comprising 20 consecutive nucleotides of a particular gene sequence will anneal to the target sequence with a higher specificity than a corresponding primer or probe of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Green and Sambrook, *Molecular Cloning, A Laboratory Manual* 4th ed. 2012, Cold Spring Harbor Laboratory; and Ausubel et al., eds., *Current Protocols in Molecular Biology*, 1994—current, John Wiley & Sons. The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", "transformed" and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subject for a period of time to one or more conditions which require the transcription of some or all of transferred polynucleotide in order for the transgenic organism or cell to live and/or grow. Polynucleotides that are transformed into a cell but are not integrated into the host's chromosome remain as an expression vector within the cell. One may need to grow the cell under certain conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A method of selecting an isolated polynucleotide that affects the level of expression of a polypeptide in a virus or in a host cell (eukaryotic, such as plant, yeast, fungi, or algae; prokaryotic, such as bacteria) may include the steps of: constructing an isolated polynucleotide of the present invention; introducing the isolated polynucleotide into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

An "expression cassette" is a nucleic acid construct, typically generated recombinantly or synthetically, which comprises a series of specified nucleic acid elements that permit transcription of a particular nucleic acid in a host cell. Typically, an expression cassette is part of an "expression vector". An expression vector or simply a "vector" is nucleic acid capable of replicating in a selected host cell or organism. An expression vector can replicate as an autonomous structure, or alternatively can integrate into the host cell chromosomes or the nucleic acids of an organelle, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector are transcribed and translated into a polypeptide or protein within the cell, organelle or organism; or any suitable construct known in the art, which comprises an "expression cassette".

The term "capable of hybridizing under stringent hybridization conditions" refers to annealing a first nucleic acid to a second nucleic acid under stringent hybridization conditions (defined below). In an exemplary embodiment, the first nucleic acid is a test sample, and the second nucleic acid is the sense or antisense strand of a nucleic acid of interest. Hybridization of the first and second nucleic acids is conducted under standard stringent conditions, e.g., high temperature and/or low salt content, which tend to disfavor hybridization of dissimilar nucleotide sequences.

Any expression vector containing the polynucleotides described herein operably linked to a promoter is also covered by this invention. A polynucleotide sequence is operably linked to an expression control sequence(s) (e.g., a promoter and, optionally, an enhancer) when the expression control sequence controls and regulates the transcription and translation of that polynucleotide sequence. An expression vector is a replicon, such as plasmid, phage or cosmid, and which contains the desired polynucleotide sequence operably linked to the expression control sequence(s). The promoter may be, or is identical to, a viral, phage, bacterial, yeast or other fungal, insect, plant, or mammalian promoter. Similarly, the enhancer may be the sequences of an enhancer from virus, phage, bacteria, blue-green algae, yeast or other fungi, insects, plants, or mammals.

"Operably linked" refers to the association of two or more nucleic acid fragments on a single polynucleotide so that the function of one is affected by the other. For example, a promoter is operably linked with a coding sequence so that the promoter is capable of affecting the expression of that coding sequence (i.e., that the coding sequence is under the transcriptional control of the promoter). Coding sequences can be operably linked to regulatory sequences in sense or antisense orientation. When a promoter is operably linked to a polynucleotide sequence encoding a protein or polypeptide, the polynucleotide sequence should have an appropriate start signal (e.g., ATG) in front of the polynucleotide sequence to be expressed. Further, the sequences should be in the correct reading frame to permit transcription of the polynucleotide sequence under the control of the expression control sequence and, translation of the desired polypeptide or protein encoded by the polynucleotide sequence. If a gene or polynucleotide sequence that one desires to insert into an expression vector does not contain an appropriate start signal, such a start signal can be inserted in front of the gene or polynucleotide sequence. In addition, a promoter can be operably linked to a RNA gene encoding a functional RNA.

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of interest in certain embodiments of the present invention are inducible-promoters for plants that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter can be induced by one or more, but not limiting to one of the following: abiotic stresses such as wounding, cold, dessication, ultraviolet-B (van Der Krol, et al., *Plant Physiol.* 121:1153-1162 (1999)), heat shock (Shinmyo, et al., *Biotechnol. Bioeng.* 58:329-332 (1998)) or other heat stress, drought stress, or water stress. The promoter may further be one induced by biotic stresses, including pathogen stress, such as stress induced by a virus (Sohal, et al., *Plant Mol. Biol.* 41:75-87 (1999)) or fungi (Eulgem, et al., *Embo J.* 18:4689-4699 (1999); Cormack, et al., *Biochim Biophys Acta* 1576:92-100 (2002)); stresses induced as part of the plant defense pathway (Lebel, et al., *Plant J.* 16:223-33 (1998)); or promoters induced by other environmental signals, such as light (Ngai, et al., *Plant J.* 12:1021-1034 (1997)), carbon dioxide (Kucho, et al., *Plant Physiol.* 121:1329-1338 (1999); Kucho, et al., *Plant Physiol.* 133:783-7893 (2003)), hormones or other signaling molecules such as auxin, hydrogen peroxide and salicylic acid (Chen, et al., *Plant J.* 19:667-677 (1999); Chen, et al., *Plant J.* 10:955-966 (1996)), sugars and gibberellin (Lu, et al., *J. Biol. Chem.* 273:10120-10131 (1998)) or abscissic acid and ethylene (Leubner-Metzger, et al., *Plant Mol. Biol.* 38:785-795 (1998)).

In other embodiments of the invention, tissue-specific promoters are used. Tissue-specific expression patterns as controlled by tissue- or stage-specific promoters that include, but are not limited to, fiber-specific, green tissue-specific, root-specific, stem-specific, root-specific, and flower-specific. Examples of the utilization of tissue-specific expression includes, but is not limit to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable. Another example of promoters that are expressed in specific tissue are chlorophyll A/B binding protein (CAB) promoter (Bansal, et al., *Proc. Natl. Acad. Sci. USA* 89(8):3654-8 (1992)), small subunit of ribulose-1,5-bisphosphate carboxylase (ssRBCS) promoter (Bansal, et al., *Proc. Natl. Acad. Sci. USA* 89(8):3654-8 (1992)), phosphoenolpyruvate carboxylase 1 (PPC1) promoter (Kausch, et al., *Plant Mol. Biol.* 45(1):1-15 (2001)), a senescence activated promoter, SEE1, (Robson, et al., *Plant Biotechnol. J.* 2(2): 101-12 (2004)), and the sorghum leaf primoridia specific promoter, RS2, (GenBank Accession No. EI979305.1).

Although many promoters from dicotyledons have been shown to be operational in monocotyledons and vice versa, in a majority of cases dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphoenol pyruvate carboxylase gene (Hudspeth, et al., *Plant Physiol.* 98:458-464 (1992)). There are suitable promoters for root specific expression (de Framond, *FEBS Lett.* 290: 103-106 (1991); Hudspeth, et al., *Plant Mol. Biol.* 31:701-705 (1996)).

A promoter selected can be an endogenous promoter, i.e., a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV). The promoter may further be, for example, a promoter for the small subunit of ribulose-1,3-bisphosphate carboxylase. Promoters of bacterial origin include the octopine synthase promoter, the nopaline synthase promoter and other promoters derived from native Ti plasmids could also be (Herrera-Estrella, et al., *Nature* 303: 209-213 (1983)). Some of these promoters are constitutive promoters for plants.

The promoters may be such that they are activated by other elements known to those of ordinary skill in the art, so that production of the protein encoded by the recombinant nucleic acid sequence may be regulated as desired. In one embodiment of the invention, a DNA construct containing a non-constitutive promoter operably linked to a polynucleotide encoding the desired polypeptide of the invention is used to make a transformed plant that selectively increases the level of the desired polypeptide of the invention in response to a signal. The term "signal" refers to a condition, stress or stimulus that results in or causes a non-constitutive promoter to direct expression of the coding sequence operably linked to it. To make such a transformed plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In another embodiment of the invention, a DNA construct comprising a SbPRH1 or SbPRH2 or both SbPRH1 and SbPRH2 operably linked to promoters that are active in root hair cells are used to make a transformed plant that selectively increases the transcript or mRNA of the desired enzyme(s) of the invention in root hair cells. However, other promoters may be used in this invention. It is understood to those of ordinary skill in the art that the regulatory sequences that comprise a plant promoter driven by RNA polymerase II reside in the region approximately 2900 to 1200 base pairs up-stream (5') of the translation initiation site or start codon (ATG). For example, the full-length promoter for the nodule-enhanced PEP carboxylase from alfalfa is 1277 base pairs prior to the start codon (Pathirana, et al., *Plant J.* 12:293-304 (1997)), the full-length promoter for cytokinin oxidase from orchid is 2189 base pairs prior to the start codon (Yang, et al., *J. Exper. Bot.* 53:1899-1907 (2002)), the full-length promoter for ACC oxidase from peach is 2919 base pairs prior to the start codon (Moon, et al., *J. Exper. Bot.* 55:1519-1528 (2004)), full-length promoter for cytokinin oxidase from orchid is 2189 base pairs prior to the start codon, full-length promoter for glutathione peroxidase1 from *Citrus sinensis* is 1600 base pairs prior to the start codon (Avsian-Kretchmer, et al., *Plant Physiol.* 135:1685-1696 (2004)), and the full-length promoter for glucuronosyltransferase from cotton is 1647 base pairs prior to the start codon (Wu, et al., *Cell Research* 17:174-183 (2007)). Most full-length promoters are 1700 base pairs prior to the start codon. The accepted convention is to describe this region (promoter) as −1700 to −1, where the numbers designate the number of base pairs prior to the "A" in the start codon.

One aspect of this invention is the transformation of fungi with the genes described here so that the transformed fungi can produce the gene products and make the compounds described herein. While one can use the some or all of the various expression vectors described herein to generate transformed fungi, one may need to use promoters that work in fungi. While some of the plant promoters described above may induce expression of foreign genes in fungi, one may want to use promoters that exist in fungi. It should not be surprising to one of ordinary skill in the art that fungal promoters, similar to plant and bacteria promoters, can be constitutive or inducible. Non-limiting examples of constitutive promoters include the following: (1) Pna2/TPI which is a hybrid promoter containing sequences from the *Aspergillus niger* neutral amylase promoter and the *A. nidulans* triose phosphate isomerase promoter (Olempska-Beer, et al., *Regul. Toxicol. Pharm* 45: 144-158 (2006)); (2) GpdA (aka GAPDH), the *A. nidulans* glyceraldehyde 3-phosphate dehydrogenase promoter (Punt, et al., *J. Biotechnol.* 17:19-34 (1991)); (3) TrpC, an *A. nidulans* tryptophan biosynthesis promoter (Hamer and Timberlake, *Mol. Cell Biol.* 7(7):2352-9 (1987)); and ToxA and ToxB promoters obtained from *Pyrenophora tritici-repentis* capable of driving expression of genes on plasmids in a variety of filamentous fungi (Andrie, et al., *Mycologia* 97:1152-1161 (2005). Additional constitutive promoters for *Saccharomyces cerevisiae* include, but are not limited to, Cyc, Adh, SteS, Pgk, Gpd, Clb, Aoxl, His4, and Tef promoters.

Non-limiting examples of inducible fungal promoters include the following: (1) TAKA-A amylase promoter from *A. oryzae* (Tada, et al., *Mol. Gen. Genet.* 229:301-306 (1991); (2) the α-amylase B (AmyB) promoter from *A. oryzae* (Hoshida, et al., *Biosci. Biotechnol. Biochem.* 69(6):1090-7 (2005); (3) the glucoamylase A (GlaA) promoter from *A. niger* (Ganzlin and Rinas, *J. Biotechnol.* 135:266-271 (2008); (4) the alcohol regulon promoters in *A. nidulans* (AlcA—alcohol dehydrogenase; AldA—aldehyde dehydrogenase; and positive regulator AlcR) (Gwynne, et al., *Biochem. Soc. Trans.* 17:338-340 (1989); and U.S. Pat. No. 5,624,046); (5) the *A. awamori* endoxylanase promoter (ExlA) (Gouka, et al., *Appl. Microbiol. Biotechnol.* 46:28-35 (1996); (6) the *A. fumigaltus* nitrite reductase promoter (NiiA) (Amaar and Moore, *Curr. Genet.* 33:206-215 (1998)); (7) the *Tricho-*

*derma reesei* cellobiohydrolase I promoter (CbhI) (Harkki, et al., *Enzyme Microb. Technol.* 13:227-233 (1991); the *Schizosaccharomyces pombe* high affinity copper transporter (Ctr4) (Bellemare, et al., *Gene* 273:191-198 (2001)); and the *A. oryzae* thiamine biosynthesis promoter (ThiA) (Shoji, et al., *FEMS Microbiol. Lett.* 244:41-46 (2005)). Additional inducible promoters for *S. cerevisiae* include Met25, Gal1, LacZ, and Kladh4. Other examples of inducible promoters are those for the heat shock, alcohol dehydrogenase, and glucocorticoid response element genes that are activated by heat, alcohol and steroid hormones respectively.

Examples of other fungal promoters include the budding yeast enolase gene (Eno1) promoter (U.S. Pat. No. 7,999, 090), the Pho5 promoter (U.S. Pat. No. 7,811,823), $UAS_{MAL}$ which is a bidirectional promoter element required for the expression of both the MAL61 and MAL62 genes of the *Saccharomyces* MALE locus (Levine, et al., *Current Genetics* 181-189 (1992), the bi-directional maltase gene promoter in *Kluyveromyces lactis* (U.S. Pat. No. 6,596,513), the bidirectional PcbAB-PcbC promoter *Acremonium chrysogenum* (Menne, et al., *Appl. Microbiol. Biotechnol.* 42:57-66 (1994)), the 3-phosphoglycerate kinase promoter (U.S. Pat. No. 5,646,012), the RP28 ribosomal protein promoter (U.S. Pat. No. 5,627,049), the transaldolase promoter (U.S. Pat. No. 5,616,474), the pyruvate decarboxylase promoter (U.S. Pat. No. 5,631,143), and the bidirectional promoter of α-aminoadipyl-cysteinyl-valine [ACV] synthetase/isopenicillin N-synthetase from *Acremonium chrysogenum* (Meme, et al., *Appl. Microbiol. Biotechnol.* 42(1):57-66 (1994)).

This invention can include recombinant bacterium is *Escherichia coli*, *Bacillus subtilus*, or *Pseudomonas* spp. that express the genes of interest and produce the encoded proteins (enzymes). Non-limiting examples of suitable bacterial promoters include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus* spp., the int promoter of bacteriophage lambda, the bla promoter of pBR322, and the CAT promoter of the chloramphenicol acetyl transferase gene. Prokaryotic promoters have been reviewed by Glick, *Ind. Microbiol.* 1:277 (1987), Watson, et al., *Molecular Biology of the Gene*, $4^{th}$ ed. (Benjamin Cummins 1987), and by Ausubel, et al. (1994).

The present invention also includes transforming blue-green algae with the DNA and expression vectors, expressing the genes, and producing the gene products and compounds described herein. As such, suitable promoters for blue-green algae include, but are not limited to, the promoters for rrnA and rrnB operons (Kumano, et al., *Molecular and General Genetics MGG* 202(2):173-178 (1986)), the promoter for RuBisCO (ribulose-1,5-diphosphate carboxylase/oxygenase) gene (U.S. Pat. No. 5,804,408), the RNA polymerase promoter from cyanophage Syn5 (Zhu, et al., *J. Biol. Chem.* 288(5):3545-3552 (2013)), the promoter of the AbrB2 gene (Dutheil, et al., *J. Bacteriol.* 194(19):5423-5433 (2012)), the psbA2 promoter from *Synechocystis* PCC6803 (Lindberg, et al., *Metabolic Engineering* 12:70-79 (2009)), and high light-inducible promoter for high light-inducible polypeptides (hliA, hliB and hliC) from *Synechocystis* PCC6803 (He, et al., *J. Biol. Chem.* 276(1): 306-314 (2001)).

The following terms are used to describe the sequence relationships between two or more nucleic acids or polynucleotides: "reference sequence", "comparison window", "sequence identity", "percentage of sequence identity", and "substantial identity". A reference sequence is a defined sequence used as a basis for a sequence comparison; a reference sequence may be a subset of a larger sequence, or gene sequence given in a sequence listing.

The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two polynucleotides or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a substantial identity exists over a region of the sequences that is at least about 50 residues in length. In another exemplary embodiment, a substantial identity exists over a region of the sequences that is at least about 100 residues in length. In still another exemplary embodiment, a substantial identity exists over a region of the sequences that is at least about 150 residues or more in length. In one exemplary embodiment, the sequences are substantially identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., *Current Protocols in Molecular Biology*, 1995 supplement).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng &

Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST® and BLAST® 2.0 algorithms, which are described in Altschul et al., Nuc. Acids Res. 25:3389-3402 (1977) and Altschul et al., J. Mol. Biol. 215:403-410 (1990), respectively. Software for performing BLAST® analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLAST® program (for nucleotide sequences) uses as defaults a wordlength (W) of 11, an expectation (E) or 10, M=5, N4 and a comparison of both strands. For amino acid sequences, the BLAST® program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST® algorithm also performs a statistical analysis of the similarity between two sequences (see, e.g., Karlin and Altschul, Proc. Natl. Acad. Sci. USA 90:5873-5787 (1993)). One measure of similarity provided by the BLAST® algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively hybridizes to" or "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Hybridization with Nucleic Probes Parts I and II*, Elsevier (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This situation can occur, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981). Using of machines for sequencing DNA or RNA is known in the art field.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994-current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, aneth, apple, apricot, artichoke, arugula, asparagus, avocado, banana, barley, beans, beech, beet, Bermuda grass, blackberry, blueberry, blue grass, broccoli, brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jatropha, jicama, kiwifruit, lettuce, leeks, lemon, lime, loblolly pine, maize, mango, melon, mushroom, nectarine, nut, oat, okra, onion, orange, an ornamental plant, palm, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, scallion, sorghum, southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include blue-green algae and other photosynthetic organisms, even if these organisms are not considered plants.

The term "plant" includes whole plants, plant organs, and progeny of same. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Some exemplary blue-green algae that can be transformed with the vectors and DNA described herein and that can produce the gene products and compounds discussed herein include, but are not limited to, *Anacystis nidulans*, *Synechococcus* spp., *Synechocystis* spp., *Spirulina platensis*, Anabaena PCC7120, Nostoc PCC7119, and Calothrix PCC7601. Transformation of blue-green algae with the expression vectors and DNA described herein can be carried out using methods known to one of ordinary skill in the art, such as those methods described in Porter, *CRC Critical Reviews in Microbiology* 13(2):111-132 (1986); Lightfoot, et al., *J. General Microbiology* 134:1509-1514 (1988); Daniell, et al., *Proc. Natl. Acad. Sci. USA* 83:2546-2550 (1986), Matsunaga, et al., *Appl. Biochem. Biotechnol.* 24/25:151-160 (1990) and Liu, et al., *Proc. Natl. Acad. Sci. USA* 108(17):6905-6908 (2011)))). It is recognized that blue-green algae are cyanobacteria and thus are considered bacteria. As discussed supra this invention includes bacteria transformed with the polynucleotides of this invention and using the recombinant bacteria to produce the encoded proteins and make the compounds disclosed herein.

In addition to plants, the polynucleotides of this invention can be transformed into fungi and the encoded proteins (enzymes) can be produced by the fungi. Non-limiting examples of suitable fungi *Saccharomyces* spp., *Pichia* spp., *Candida* spp., *Aspergillus* spp., or *Kluyveromyces* spp. More specifically, one can utilize *S. cerevisiae*, *P. pastoris*, *P. methanolica*, *C. albicans*, *A. niger*, or *Kluyveromyces lactis* for this invention.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

EXAMPLE 1

Identification of ESTs with Putative Cytochrome P450 Domains

Sorghum root-hair EST database mining is performed as described in Baerson, et al., J. Biol. Chem. 283:3231-3247 (2008) and Cook, et al., (2010). All ESTs have been deposited in GenBank and have been incorporated into the current NCBI unigene release (build #27, 2 Mar. 2008). Fourteen cytochrome P450-like sequences on ESTs are identified by BLASTN® and TBLAST® analysis (Altschul, et al., (1997)). These sequences are assembled into eleven unique sequences by cluster analysis, eight of which are represented by a single EST (i.e., singletons).

EXAMPLE 2

Identification of Root Hair Cell Expressed Putative Cytochrome P450 Genes

To identify the cytochrome P450 sequences where are expressed specifically or predominantly in root hair cells of *S. bicolor*, quantitative real-time PCR (qRT-PCR) is performed using cDNAs prepared from total RNA isolated from root hairs, root systems, developing panicles, stems, immature and fully expanded leaves, and shoot apices. *S. bicolor* seeds are purchased from Crosbyton Seed Company (Crosbyton, Tex.) and grown according to conditions set forth in Cook, et al. (2010). Mature leaves, stems and emerging panicles are harvested from approximately two-month old, greenhouse-grown *S. bicolor* plants. Immature leaves and shoot apices are isolated from eight-day old seedlings maintained in a growth chamber at 28° C., 16 hours light and 8 hours dark, 400 µmol/m²sec intensity. Total root systems and root hairs are isolated from 8-day old seedlings grown using a capillary mat system. All tissue collected is flash-frozen in liquid nitrogen and kept at −80° C. until RNA extraction. Root hairs are isolated according to the protocol set forth in Bucher, et al., *Plant Mol. Biol.* 35:497-508 (1997). Total RNA for qRT-PCR and cDNA cloning are extracted from the previously flash-frozen *S. bicolor* tissues using TRIzol® Reagent (Life Technologies, Carlsbad, Calif.) using the protocol described in Cook, et al., 2010. Briefly, frozen plant tissues are homogenized using a handheld homogenizer (homogenization step of 30 seconds at 25,000 rpm) which is followed by RNA purification with an RNeasy Plant Mini Kit (Qiagen, Valencia, Calif.) according to the manufacturer's instructions. Isolated RNAs are further treated with RNase-free DNase to remove residual DNA contamination (Qiagen, Valencia, Calif.). The purity of RNAs is determined spectrophotometrically, and the integrity of purified RNAs is also assessed by agarose gel electrophoresis. qRT-PCR reactions are performed in triplicate using a model 7300 Sequence Detection System (Applied Biosystems, Carlsbad, Calif.) as previously described (Cook, et al., 2010). PCR primers were designed using Primer Express® v2.0 software (Applied Biosystems, Foster City, Calif.) and the Amplify program (Engels, W. R. 1993. *Trends Biochem. Sci.* 18: 448-450). A dissociation curve is generated at the end of each PCR cycle to verify that a single product is amplified using software provided with model 7300 Sequence Detection System. A negative control reaction minus cDNA template (non-template control) is also routinely performed in triplicate for each primer pair. The change in fluorescence of SYBR® Green I dye in every cycle is monitored by the GenAmp® 7300 system software, and the threshold cycle ($C_T$) above background for each reaction is calculated. The $C_T$ value of 18S rRNA is subtracted from that of the gene of interest to obtain a $\Delta C_T$ value. The $C_T$ value of an arbitrary calibrator (e.g., the tissue sample from which the largest $\Delta C_T$ values are obtained) is subtracted from the $\Delta C_T$ value to obtain a $\Delta\Delta C_T$ value. The fold-changes in expression level relative to the calibrator are calculated as $2^{-\Delta\Delta C_T}$. The gene specific PCR primer pairs used for the 18s rRNA and three candidate P450s are listed in Table 1 below.

TABLE 1

| Primer | Name | Primer pairs (5'->3') |
|---|---|---|
| 21G12 forward | RTHAIR1_21_G12.g1_A002 | AAGATCCAAGGCTACCATGTGC (SEQ ID NO: 1) |
| 21G12 reverse | RTHAIR1_21_G12.g1_A002 | AACGTTGGCGACGACTATTG (SEQ ID NO: 2) |
| 69C05 forward | RTHAIR1_69_C05.g1_A002 | CCACTTTGATTGGTCCCTGC (SEQ ID NO: 3) |
| 69C05 reverse | RTHAIR1_69_C05.g1_A002 | TCTGTCATGTCAACCTCATCGAC (SEQ ID NO: 4) |
| 18S forward | 18s rRNA | GGCTCGAAGACGATCAGATACC (SEQ ID NO: 5) |
| 18S reverse | 18s rRNA | TCGGCATCGTTTATGGTT (SEQ ID NO: 6) |

Figure 2:
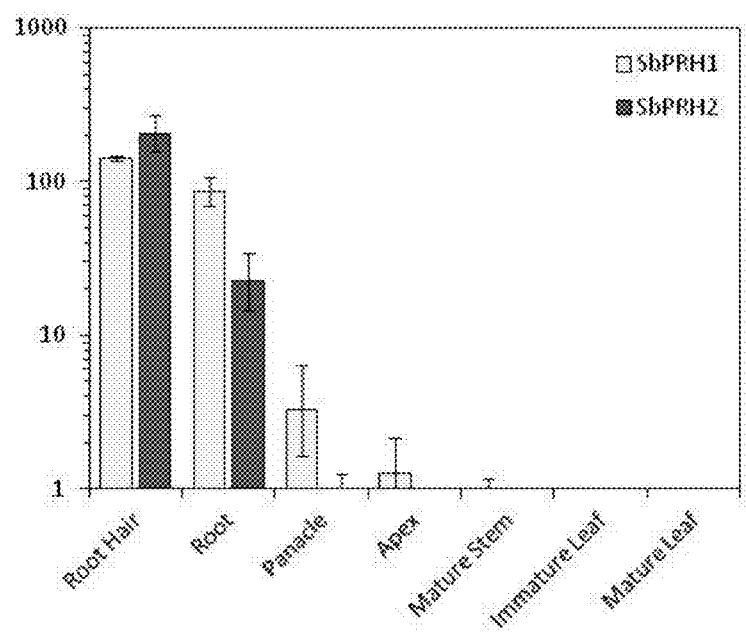
FIG. 2 shows the levels of expression of SbPRH1 and SbPRH2 in various plant tissues as determined by qRT-PCR.
Figure 3A:
FIGS. 3A, 3B, 3C, and 3D show the extracted ion chromatogram (EIC) for the ion m/z 400 and 576 of dihydrosorgoleone (FIG. 3A), yeast transformed with CYP71AM1 (FIG. 3B) or CYP71V7 (FIG. 3C), and negative control yeast transformed with empty vector (FIG. 3D), demonstrating that the yeast transformed with CYP71AM1 or with CYP71V7 convert 3-methyl-5-pentadecatrienyl resorcinol to dihydrosorgoleone. The EIC is shown detailing a single intense peak at 13.03 min for TMS derivatized substrate (m/z=400) and 14.16 min for dihydrosorgoleone (m/z=576).
Figure 3B:
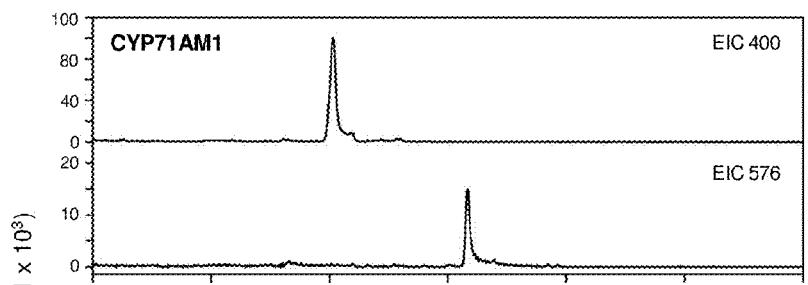
Figure 3C:
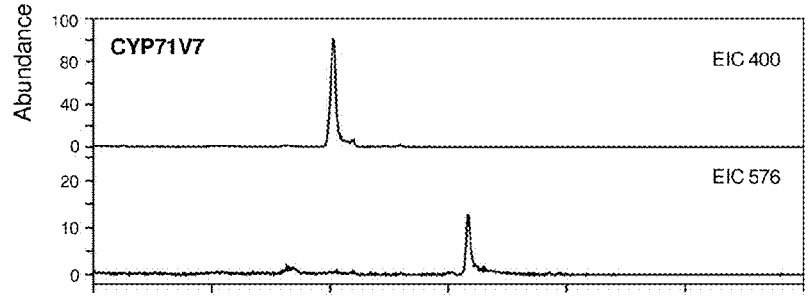
Figure 3D:
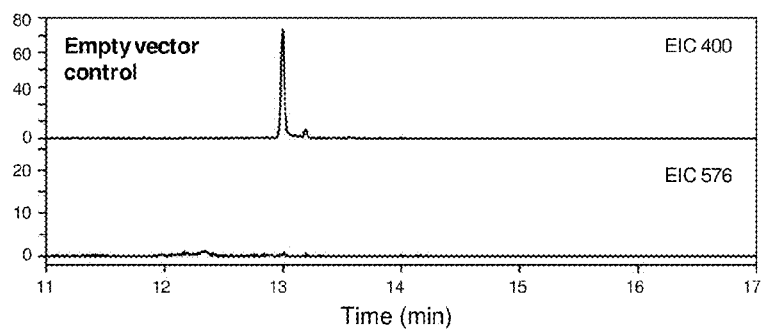

The sequences covered by each of these three primer sets are preferentially expressed in root hair cells and slightly less so in root systems. See FIG. 2 for levels of expression in various plant tissue as determined by qRT-PCR.

EXAMPLE 3

Generation of cDNA of the Root Hair Cell Expressed Genes

To obtain full-length cDNA clones of the three root hair cell expressed genes, partial sequences for *S. bicolor* RTHAIR1_21_G12.g1_A002 and RTHAIR1_69_C05.g1_A002 (designated 21G12 and 69C05, respectively) obtained from previously generated root hair EST assemblies (Baerson, et al. (2008)) are used for both 5'- and 3' rapid amplification of cDNA ends (RACE) using the BD SMART™ RACE cDNA Amplification Kit (Clontech, Palo Alto, Calif.) according to the manufacturer's instructions. Primer sets for 5'- and 3'-RACE are as follows: for 21G12, toward the 5' end primer 5'-TGGGACGAACGGGGCAG-GAG-3' (SEQ ID NO: 7) and toward the 3' end primer 5'-GGCATCAAGATCCAAGGCTAC-3' (SEQ ID NO: 8); and for 69CO₅, toward the 5' end primer 5'-TCATGTCAAC-CTCATCGACACC-3' (SEQ ID NO: 9) and toward the 3' end primer 5'-TCTACCACTTTGATTGGTCCCTG-3' (SEQ ID NO: 10). Full-length cDNAs are then amplified with primer pairs complementary to the 5'- and 3'-UTRs identified in RACE experiments using PfuUltra DNA polymerase (Stratagene, La Jolla, Calif.) and first-strand cDNA generated from RNA extracted from sorghum root hairs. Several independent isolates from each amplification are sequenced to ensure the authenticity of the open reading frames. The DNA sequence of SbPRH1 is in SEQ ID NO: 11, and the deduced amino acid sequence is in SEQ ID NO: 12. The DNA sequence of SbPRH2 is in SEQ ID NO: 13, and the deduced amino acid sequence is in SEQ ID NO: 14.

The amino acid sequences which are deduced from SbPRH1 and SbPRH2 are 40.0% identical to each other. BLASTP® analysis of these two amino acid sequences reveal that neither sequences exhibit extensive similarity to known functionally characterized plant P450 sequences. The amino acid sequences of SbPRH1 and SbPRH2 correspond to typical plant P450 family members of the CYP71 class, i.e., CYP71AM1 and CYP71V7, respectively. These nomenclatures will be used for these genes hereafter. The predicted amino acid sequences of the cDNA clones exhibit all of the major elements typically found in plant cytochrome P450 monooxygenases, such as the proline-rich region, the O2 binding site, and the PERF-motif located upstream of the heme-binding cysteine motif (Bak, et al., "Cytochrome P450" in The Arabidopsis Book v.9 ISSN: 1543-8120 published by The American Society of Plant Biologists (2011)).

A third party previously performed genomic sequencing of *S. bicolor* and deposited the sequence of putative genes and putative proteins in GenBank. The DNA sequences of SbPRH1 (CYP71AM1) is similar to the DNA sequence of a hypothetical gene at GenBank accession number XM_002451987, and the putative amino acid sequences of the two are completely identical. The DNA sequences of SbPRH2 (CYP71V7) is similar to the DNA sequence of a hypothetical gene at GenBank accession number XM_002465028, and the putative amino acid sequences of the two are completely identical. It is worth noting that the investigators who deposited the sequences in GenBank did not perform experiments to confirm that the presumed DNA sequence actually is a full-length gene and is transcriptionally active in *S. bicolor*. Nor did the investigators determine the activity of the putative protein. In light of the information contained in Example 7 below, simply identifying a putative gene encoding a putative cytochrome P450 does not mean that one knows the activity of the encoded enzyme.

EXAMPLE 4

Recombinant Constructs for Heterologous Expression in *S. Cerevisiae*

To examine whether these sorghum P450s possesses dihydroxylation activity towards 3-methyl-5-pentadecatrienyl resorcinol, a methylated resorcinolic intermediate in the sorgoleone biosynthetic pathway, one needs to perform functional expression in yeast. Two plasmids, pYeG12 carrying CYP71AM1 and pYeC05 carrying CYP71V7, are constructed by inserting the full-length cDNA into the yeast expression vector pYeDP60 plasmid that allows galactose-inducible expression of P450s in yeast (Pompon, et al. (1996)). For heterologous expression in yeast, open reading frames are amplified using PfuUltra DNA polymerase (Stratagene, La Jolla, Calif.) and cloned in the pYeDP60 vector (Pompon, et al., *Methods Enzymol.* 272:51-64 (1996)) using the BamHI and KpnI restriction sites, yielding the plasmids pYeG12 (for 21G12) and pYeC05 (for 69C05). For pYeG12, the forward primer is CYP71AM1F3 5'-TACCATGGAC-GAATACTTTGTTGACCTGC-3' (SEQ ID NO: 15), and the reverse primer is CYP71AM1R35'-TTATGCATCAATC-GATGCAGCAGCTG-3' (SEQ ID NO: 16). For pYeC05, the forward primer is CYP71V7F3 5'-TACCATGGAAGTGT-TCCAACCCCTCC-3' (SEQ ID NO: 17), and the reverse primer is CYP71V7R35'-CTAGCTTGGCACCCTGCTG-GTTTC-3' (SEQ ID NO: 18). The constructs are then transformed into the *S. cerevisae* WAT11 strain (Pompon, et al. (1996)) using the lithium acetate method (see Burke, et al., *Methods in Yeast Genetics*, (Cold Spring Harbor Labs, NY, 2000). Briefly, yeast are grown overnight in a 30° C. shaker in 10 ml complete YPGA liquid medium [10 g/L yeast extract (Difco), 10 g/L bactopeptone (Difco) 20 g/L glucose, 200 mg/L adenine] to an $OD_{600}$ between 1.0 and 1.5. The cells are collected by centrifugation at 2500×g for 5 minutes at 4° C., and are resuspended in 1.5 ml of a 0.1 M lithium acetate (LiAc) solution in TE buffer (10 mM Tris-HCl, pH 7.5, 1 mM EDTA). A 0.12 ml aliquot of cells in a 1.5-ml Eppendorf tube is used for transformation. Plasmid DNA (1 μg in 10 μl TE buffer) and salmon sperm DNA as DNA carrier (100 μg from a 10 mg/ml solution in TE after 5 minutes boiling) are added to the competent yeast cells. 500 μl of 40% polyethylene glycol 3350 in 0.1 M LiAc solution in TE buffer and 57 μl DMSO are added. The mixture is incubated for 15 minutes at room temperature, then for 15 minutes at 42° C. After centrifugation for 10 seconds at 10,000×g the transformed yeast cells are resuspended in 200 μl TE buffer, and then are plated on SGI minimal media [7 g/L yeast nitrogen base; 20 g/L glucose; 20 mg/L tryptophan; 20 g/L agar (Difco)]. All yeast transformants are confirmed by colony-PCR using gene-specific primers, and by further restriction analyses performed using isolated plasmid preparations.

EXAMPLE 5

Preparation of Yeast Microsomes

Microsomes are prepared according to the method described by Pompon, et al. (1996). Colonies from strains transformed with pYeDP60 and the two P450 constructs are transferred using sterile toothpicks into 15 ml SGI minimal media (1 g/L bacto casamino acids, 7 g/L yeast nitrogen base, 20 g/L glucose, and 20 mg/L tryptophan) and are grown overnight at 30° C. to a density of $6 \times 10^7$ cells per nil. This pre-culture is diluted into 250 ml YPGE (5 g/L glucose, 10 g/L yeast extract, 10 g/L bactopeptone, 3% [v/v] ethanol) to a density of $2 \times 10^5$ cells per nil, and is grown until it reaches a density of $8 \times 10^7$ cells per ml (approximately 30 h). The culture is centrifuged, and the pellet is resuspended in 250 ml YPI induction medium (10 g/L yeast extract, 10 g/L bactopeptone 20 g/L galactose) and grown for 16 hours at 30° C. Microsomal membranes are isolated after mechanical disruption of yeast cells with glass beads (Pompon, et al. (1996)). Microsomal protein concentrations are determined using a Bio-Rad protein assay kit (Bio-Rad, Hercules, Calif.) with bovine serum albumin as a standard. Dithionite-reduced, carbon monoxide difference spectra are obtained using an Evolution 300 spectrophotometer (Thermo Scientific, Somerset, N.J.) according to the method described by Guengerich, et al., *Nat. Protoc.* 4:1245-1251 (2009). Microsomes from yeast transformed with vector pYeDP60 alone are used as negative controls.

The recombinant proteins are expressed in the *S. cerevisae* WAT11 strain that co-expresses the NADPH-cytochrome P450 reductase gene from *Arabidopsis thaliana* (Urban, et al., *Biochimie* 72:463-472 (1990); Pompon, et al. (1996)). The P450 functional expression is determined at 450 nm using a carbon monoxide (CO) differential spectrum. The CO difference spectrum with a characteristic peak at 450 nm is obtained from microsomal fractions extracted from yeast expressing CYP71AM1 and CYP71V7, indicating the presence of a functional cytochrome P450. The CO difference spectrum of microsomal fractions extracted from the empty vector negative control yeast lack a peak at 450 nm.

EXAMPLE 6

In Vivo Assay of Recombinant Cytochrome P450s

For functional analysis of these recombinants, one colony is inoculated into 5 ml SGI and grown at 30° C. with shaking (250 rpm) for approximately 24 hours. The cell culture is then transferred to 50 ml fresh SGI, and the cells are grown at 30° C. for 24 hours with shaking at 250 rpm. The cells are collected by centrifugation at 500×g for 5 minutes. The cell pellet is resuspended in 20 ml of galactose-containing induction medium (5 g/L yeast extract, 5 g/L bacto peptone, 20 g/L galactose and 1% tergitol Nonidet P40 (Sigma Aldrich, St.

Louis, Mo.)). Substrate (3-methyl-5-pentadecatrienyl resorcinol, synthesized in-house) is added to a final concentration of 0.2 mM. Cells are allowed to continue growing at 28° C. for 16 hours, then are harvested by centrifugation at 1500×g for 5 minutes. The cell pellet is washed with 10 ml of 10 mM $K_3PO_4$ (potassium phosphate) buffer, pH 7.5. Cells are then treated for 10 minutes in a Branson ultrasonic water bath (Branson, Danbury, Conn.) with 10 ml methanol. The mixture is clarified by centrifugation at 1,000×g for 10 minutes. The methanol phase is recovered and is dried under vacuum. The dried extracts are treated with 100 μl of N,N-bis(trimethylsilyl)trifluoroacetamide (BSTFA) in an oven at 125° C. for 1 hour. The treated extracts then are clarified by centrifugation at 13,000 rpm for 1 minute, and the clear upper phase is recovered for GC-MS analysis.

GC-MS analysis is performed with an HP 6890 GC system equipped with a Hewlett-Packard HP-5 capillary column (Hewlett Packard, Palo Alto, Calif.) under the following oven conditions: an initial oven temperature of 120° C. for 2 minutes and a ramp of 20° C./minute to a final temperature of 300° C. which is held for 18 minutes. Total run time is 29 minutes. One microliter aliquots of BSTFA-derivatized extracts are injected directly into the gas chromatograph.

Figure 4A:
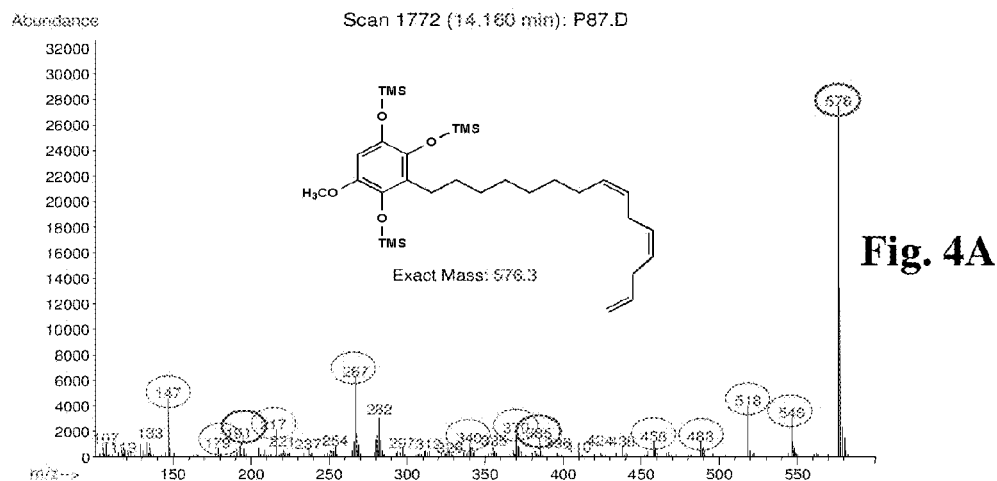
FIGS. 4A, 4B, and 4C are the mass spectra of TMS-derivatized products.
Figure 4B:
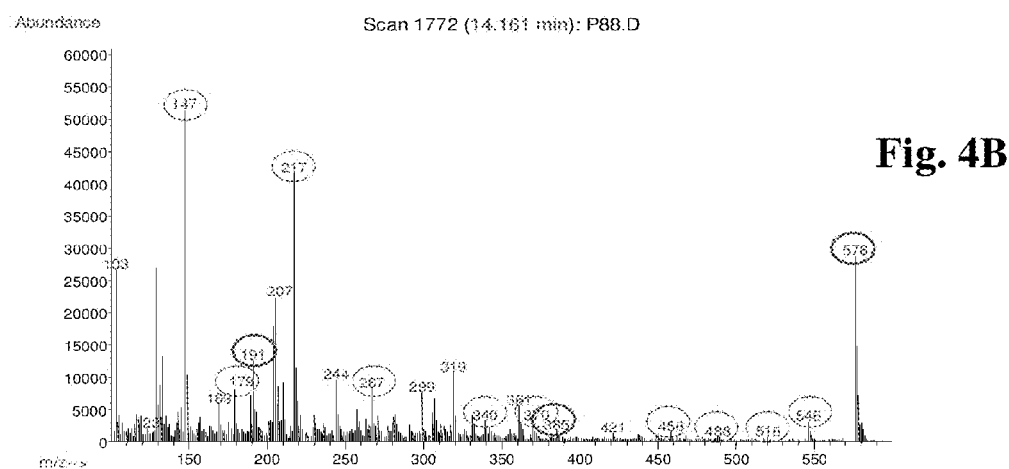
Figure 4C:
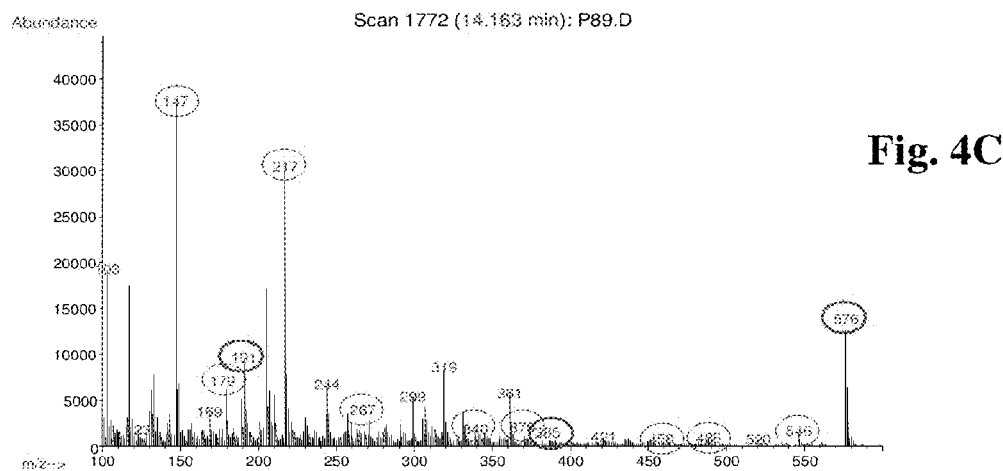

Induced cultures of the yeast transformants are incubated with the predicted substrate, 3-methyl-5-pentadecatrienyl resorcinol, and the products are analyzed by GC-MS (FIG. 3). As a control, strains harboring the empty pYeDP60 vector are cultured in parallel. As seen in FIGS. 3B and 3C, expressing CYP71AM1 or CYP71V7 in yeast with this substrate results in the appearance of a new peak with a retention time of 14.16 minutes and the derivatized parent ion mass of 576 (FIG. 3), corresponding to the calculated molecular mass. When 3-methyl-5-pentadecatrienyl resorcinol is incubated with recombinant yeast strains producing sorghum CYP71AM1 or CYP71V7 (FIGS. 3B and 3C), the added substrate with a peak at 13.03 min is metabolized to produce the reduced form of sorgoleone having a peak at 14.16 minutes, which is comparable to the chromatogram generated from authentic dihydrosorgoleone (FIG. 3A), confirming that CYP71AM1 and CYP71V7 have dihydroxylation activity. Moreover, the ion fragments of the new peak observed in the mass spectrum are consistent with the fragmentation of the dihydrosorgoleone standard (FIG. 4). Taken together, these results indicate that both CYP71AM1 and CYP71V7 have pentadecatrienyl resorcinol hydroxylase activity and each encoded enzyme are capable of hydroxylating 3-methyl-5-pentadecatrienal resorcinol at position 4 and 6, resulting in the conversion of the resorcinol into dihydrosorgoleone (a hydroquinone), the direct precursor of sorgoleone (a benzoquinone). The identification and functional characterization of CYP71AM1 and CYP71V7 extends the known range of activities associated with the cytochrome P450 CYP71 family of enzymes.

EXAMPLE 7

Other Cytochrome P450 Enzyme Isolated Lacking Appropriate Enzymatic Activity

A third EST for which the polynucleotide sequence contained cytochrome P450 domains is isolated according to Example 1. Using the experimental protocol set forth in Example 2 but with primers specific for this gene, it is determined that this gene is expressed in both roots and root hair cells. Using the protocol set forth in Example 3, but using primers specific for this gene, a cDNA of the gene is obtained and then is sequenced. The DNA sequence of this gene is 49.3% identical to the sequence of SbPRH1 and only 44.1% identical to the sequence of SbPRH2. These percentage identity to SbPRH1 and SbPRH2 are approximately similar to the percentage identity that SbPRH1 shares with SbPRH2. Using the protocol of Example 4, again with its own set of primers, this gene is cloned into the pYeDP60 expression vector and transfected into *S. cerevisiae*. P450 functional expression using a carbon monoxide differential spectrum at 450 nm per the protocol of Example 5 fails to produce a peak at 450 nm for this other gene product. Furthermore, in-vivo assays of the recombinant yeast containing the cDNA encoding this other gene (as set forth in Example 6) fails generate data via GC-MS that demonstrates that the enzyme encoded by this cDNA metabolizes 3-methyl-5-pentadecatrienyl resorcinol to dihydrosorgoleone. While one may have expected the enzyme encoded by the cDNA would have similar activity as SbPRH1 and SbPRH2, it is demonstrated that the encoded enzyme does not possess the same activity, even though it contains approximately the same sequence homology to both SbPRH1 and SbPRH2 as SbPRH1 and SbPRH2 have to each other.

EXAMPLE 8

Expression of Multiple Sorgoleone Biosynthetic Enzymes in Transgenic Plants

Crops, such as maize (*Zea mays*), rice (*Oryza sativa*), soybean (*Glycine max*), and others, may be genetically engineered to produce sorgoleone or sorgoleone analogues through the expression of genes associated with the sorgoleone biosynthetic pathway. To generate such transgenic plants expressing multiple genes, one uses a binary vector containing multiple transgene expression cassettes, with each cassette containing, at a minimum, a gene promoter, a full-length open reading frame of the transgene, and a polyadenylation or terminator region. To obtain transgenic plants capable of producing dihydrosorgoleone, five genes (or transgenes) are used to transform the plant in question: two fatty acid desaturases (SbDES2 and SbDES3; U.S. Pat. No. 8,383, 890), an alkylresorcinol synthase (either SbARS1 or SbARS2; U.S. Patent Pub. 2011-0225676), an O-methyltransferase (SbOMT3; U.S. Pat. No. 7,732,666), and either of the two cytochrome P450 enzymes discussed supra, SbPRH1 (SEQ ID NO: 11) or SbPRH2 (SEQ ID NO: 13). In the present example, a binary vector system developed by Tzfira, et al., *Plant Mol. Biol.* 57: 503-516 (2005) is used for the expression of an intact sorgoleone biosynthetic pathway in transgenic plants. However, one can use any of several other vector systems for the assembly of multi-gene expression cassettes within a binary vector (e.g., Lin, et al., *Proc. Natl. Acad. Sci. USA*, 100(10), 5962-5967 (2003); Tzfira, et al., 2005; Chung, et al., *Trends in Plant Science*, 10(8): 357-361 (2005); Schmidt, et al., *In Vitro Cell. Dev. Biol.-Plant*, 44:162-168 (2008)).

The SbARS1 and SbARS2 enzymes possess identical biochemical functions, and similarly, the SbPRH1 and SbPRH2 enzymes possess identical biochemical functions, thus only one cDNA encoding each enzyme type is used in the present example. The open reading frames (ORFs) of SbDES2, SbDES3, SbARS1, SbOMT3 and SbPRH1 are first individually PCR-amplified using PfuUltra™ II Fusion HS DNA Polymerase (Agilent Technologies, Santa Clara, Calif.), using cDNA clones as template and gene-specific PCR primers as provided above or in the above cited references and using PCR reaction conditions described above or in the above cited references. The PCR-amplified products are individually subcloned into the intermediate shuttle vector pSAT4 (GeneBank Accession number: DQ005466, Chung, et al. (2005)), generating the following five individual plasmids: 1) pSAT4-DES2 (35S promoter-SbDES2-35S terminator), 2) pSAT4-DES3 (35S promoter-SbDES3-35S terminator), 3) pSAT4-SbARS1 (35S promoter-SbARS1-35S terminator), 4) pSAT4-SbOMT3 (35S promoter-SbOMT3-35S terminator), and 5) pSAT4-SbPRH1 (35S promoter-SbPRH1-35S terminator).

Each expression cassette is then amplified from these intermediate shuttle plasmids by PCR using primer pairs containing recognition sites for different rare-cutting restriction endonucleases. In particular, the amplicon generated for the expression cassette containing the 35S promoter-SbDES2-35S terminator is flanked by recognition sites for the restriction enzyme I-PpoI; the 35S promoter-SbDES3-35S terminator is flanked by recognition sites for I-SceI; the 35S promoter-SbARS1-35S terminator is flanked by recognition sites for I-CeuI; the 35S promoter-SbOMT3-35S terminator is flanked by recognition sites for PI-PspI; and the 35S promoter-SbPRH1-35S terminator is flanked by PI-TliI recognition sites. The expression cassettes are then assembled into the multiple cloning site (MCS) of the Agrobacterium binary vector pRCS2 (GeneBank Accession number: DQ005454, Chung, et al. (2005)) using the existing compatible sites. The PCR amplicons containing the various expression cassettes are first digested with the appropriate restriction enzymes and are then ligated to similarly-treated pRCS2, sequentially, resulting in all of the five cassettes stacked within the T-DNA of a single binary vector. Prior to stacking these gene cassettes into pRCS2, the vector requires modification in order for the expression of the selectable marker bar gene (coding for phosphinothricin acetyl transferase) to be driven by the CaMV 35S promoter. To accomplish this, the 35S Pro-bar-T35 cassette is first amplified from the plasmid pLH7000 (Hausmann and Toepfer, Development of Plasmid Vectors. In Bioengineering of Custom-Tailored Rape Varieties, D. Brauer, G. Roebbelen, and R. Toepfer, eds (Goettingen, Germany: Gesellschaft fuer Pflanzenzuechtung), pp. 155-171 (1999)) using PCR primers containing recognition sites for the restriction enzyme AscI. The resulting PCR product is then treated with AscI and ligated to the AscI-treated pRCS2 backbone (which includes pRCS2 minus the Pocs-bar-Tocs cassette). The final binary vector containing all five expression cassettes is confirmed by DNA sequence analysis, and then is mobilized into Agrobacterium tumefaciens strain LBA4404 (but strains EHA 101 or EHA 105 can also be used) for plant transformation.

To express the five sorghum gene products specifically in root hair cells of transgenic plants, three published root hair-specific promoter sequences, AtEXP7 (Cho and Cosgrove, Plant Cell, 14:3237-3253 (2002)), OsEXPA17 (Yu, et al., The Plant Journal 66:725-734 (2011)) and OsCSLD1 (Kim, et al., Plant Physiology, 143:1220-1230 (2007)) are employed. The promoter sequences are first amplified from either Arabidopsis (ecotype Col-0) genomic DNA (AtEXP7 promoter) or rice genomic DNA (cv. Dongjin for the OsCSLD1 promoter; cv. Kasalath for the OsEXPA17 promoter) using gene-specific primers. The promoter sequences (AtEXP7 promoter: 2500 bp; OsEXPA17 promoter: 2563 bp; OsCSLD1 promoter: 2500 bp) obtained by PCR are then cloned into the pCR-Blunt II-TOPO vector (Life Technologies, Grand Island, N.Y.) for sequencing to confirm their authenticity. These three promoter sequences are next used to generate the final root hair-specific expression cassettes. The 35S promoter sequences used to direct the expression of each sorghum gene product in the intermediate shuttle vectors (pSAT4 derived vectors) described above are replaced with root-hair specific promoters using standard cloning procedures. For example, the 35S promoter of the 35S promoter-SbDES2-35S terminator expression cassette is replaced by the AtEXP7 promoter, resulting in an AtEXP7 promoter-SbDES2-35S terminator cassette with flanking recognition sites for restriction enzyme I-PpoI. Likewise, the 35S promoter in the 35S promoter-SbDES3-35S terminator cassette is replaced by the OsEXPA17 promoter to generate an OsEXPA17 promoter-SbDES3-35S terminator cassette with flanking I-SceI recognition sites. A similar approach is used to generate an OsCSLD1 promoter-SbARS1-35S terminator cassette with flanking I-CeuI sites, an AtEXP7 promoter-SbOMT3-35S terminator cassette with flanking PI-PspI sites, and an OsCSLD1 promoter-SbPRH1-35S terminator cassette with flanking PI-TliI sites. These expression cassettes are then assembled into the MCS of the modified binary vector pRCS2 described above. The complete binary vector containing all five transgene expression cassettes is mobilized into A. tumefaciens strain LBA4404 (but strains EHA 101 or EHA 105 can also be used) for plant transformation.

Transgenic rice, maize and soybean plants are generated using Agrobacterium tumefaciens strains harboring the binary vectors described above using previously-described methods (for rice: Hiei, et al., The Plant Journal 6(2):271-282 (1994) and Toki, Plant Molecular Biology Reporter 15:16-211997; for maize: Frame, et al., Plant Physiology 129:13-22 (2002); and for soybean: Paz, et al., Plant Cell Reports 25:206-213 (2006)). Other plant species are also amenable to the above-described procedures, or amenable following minor modifications of the above procedures.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
```
aagatccaag gctaccatgt gc                                           22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aacgttggcg acgactattg                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccactttgat tggtccctgc                                              20

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tctgtcatgt caacctcatc gac                                          23

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggctcgaaga cgatcagata cc                                           22

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
tcggcatcgt ttatggtt                                                18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tgggacgaac ggggcaggag                                              20

<210> SEQ ID NO 8
<211> LENGTH: 21
<212> TYPE: DNA

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 8
ggcatcaaga tccaaggcta c                                           21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tcatgtcaac ctcatcgaca cc                                          22

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tctaccactt tgattggtcc ctg                                         23

<210> SEQ ID NO 11
<211> LENGTH: 1644
<212> TYPE: DNA
<213> ORGANISM: Sorghum bicolor

<400> SEQUENCE: 11
gaggcagtgt gttgcaacta acaccatgga cgaatacttt gttgacctgc catacccaaa      60
cttatgcttg tacggctcct gcctcgtgct tgcagtcgtc gtcgcccgtg ccatcatcct     120
cagcggcagc ggcaagaaac caggtggcct gcctccgggc ccatggcagt taccggtgat     180
cggcagcctc caccacctgc tgcggggggct cccgcaccac gccatccgcg acctgtccct     240
gcgtcacggc ccgctgatgc tgctaaggat ctgcgagcgc acggccatcg tggtgtcctc     300
cgctgaggcc gtggcggaga tgttgaagcg ccacgacgcc gccttctcgg agcggccgag     360
cagcccgggc atcgaggagc tgtcgaggca cgggcaggga gtcatcttcg cgccctacgg     420
cgaccactgg cgcctgctgc ggcggatcct catgacggag ctgctgagcc gcggcgcgt     480
ggaggcgttc cggcacatcc gcgaggacga ggcggctcgc ctggtctcgt cgctgtcgtc     540
cctgcctcag cccgtcgaca tggacgagcg gctggaggtg ttcgtcgccg actcctccgt     600
gcgcgccatc ttgggcgacc ggttgcccga ccgcgccgcg ttcctgaaga tggtcaaggc     660
agggcaggac ccgtcgtcgc tgttcgacct ccgcgacctg ttcccgtcgt cgtggctcgt     720
gcggatgctg ccgcggagcc gcaaggcgga gcggcacctc caggagatgt tccggctcat     780
ggacgacatc ctcgtgagcc acagccaaag gagggtcgac gatgatagcc agacggggg      840
cggtggtggc gccgtcgacg aggagcatga catggtggac gttctgctca ggatccagaa     900
gcaaggcgac atgcgtgttt ctctcaacca tggagtcatc agggcggcgc tcatagatgc     960
ggttggtgca gcacttgaca caacatcgac taccctccgg tgggctatgg ccgaactaat    1020
cgcaaaccca aggtgatgc acaaggcgca gcttgagatt cgacgcgtca tggcagctgg     1080
gcaacaacga cgagtacatg aggcgactct aagggaccta cactacctga aagcagtgat    1140
caaagagacc ttacgactgc acccctcctgc cccgttcgtc ccaagggtat gcttggatga    1200

```
tggcatcaag atccaaggct accatgtgcc gcggggggaca atagtcgtcg ccaacgtttg    1260
ggctatttcc agggacccaa agtactggga ggacccagac atgtttatac agagagatt    1320 tcatcagggt gaccccgacc accaccgctg tttcgacttc aagggggttcg attttgagtt    1380 cactcctttc ggggctgggc gcaggatgtg ccccgggatg aatttcgctc atatgaacgt    1440
tgagattgct ctggctagcc tcctgtacca ctttgactgg aagctgccag atggagctac    1500
accggaggag attgacatga cagagctctg gggcgttact gtcgctagga aggctaagct    1560
acttttacat cccattcctt gtattccagc tgctgcatcg attgatgcat aaaatatttc    1620
cattcacaca aataataaaa taaa                                           1644

<210> SEQ ID NO 12
<211> LENGTH: 528
<212> TYPE: PRT
<213> ORGANISM: Sorghum bicolor

<400> SEQUENCE: 12

Met Asp Glu Tyr Phe Val Asp Leu Pro Tyr Pro Asn Leu Cys Leu Tyr
1               5                   10                  15

Gly Ser Cys Leu Val Leu Ala Val Val Ala Arg Ala Ile Ile Leu
            20                  25                  30

Ser Gly Ser Gly Lys Lys Pro Gly Gly Leu Pro Pro Gly Pro Trp Gln
        35                  40                  45

Leu Pro Val Ile Gly Ser Leu His His Leu Leu Arg Gly Leu Pro His
    50                  55                  60

His Ala Ile Arg Asp Leu Ser Leu Arg His Gly Pro Leu Met Leu Leu
65                  70                  75                  80

Arg Ile Cys Glu Arg Thr Ala Ile Val Val Ser Ser Ala Glu Ala Val
                85                  90                  95

Ala Glu Met Leu Lys Arg His Asp Ala Ala Phe Ser Glu Arg Pro Ser
            100                 105                 110

Ser Pro Gly Ile Glu Glu Leu Ser Arg His Gly Gln Gly Val Ile Phe
        115                 120                 125

Ala Pro Tyr Gly Asp His Trp Arg Leu Leu Arg Arg Ile Leu Met Thr
    130                 135                 140

Glu Leu Leu Ser Pro Arg Arg Val Glu Ala Phe Arg His Ile Arg Glu
145                 150                 155                 160

Asp Glu Ala Ala Arg Leu Val Ser Ser Leu Ser Ser Leu Pro Gln Pro
                165                 170                 175

Val Asp Met Asp Glu Arg Leu Glu Val Phe Val Ala Asp Ser Ser Val
            180                 185                 190

Arg Ala Ile Leu Gly Asp Arg Leu Pro Asp Arg Ala Ala Phe Leu Lys
        195                 200                 205

Met Val Lys Ala Gly Gln Asp Pro Ser Ser Leu Phe Asp Leu Arg Asp
    210                 215                 220

Leu Phe Pro Ser Ser Trp Leu Val Arg Met Leu Pro Arg Ser Arg Lys
225                 230                 235                 240

Ala Glu Arg His Leu Gln Glu Met Phe Arg Leu Met Asp Asp Ile Leu
                245                 250                 255

Val Ser His Ser Gln Arg Arg Val Asp Asp Asp Ser Pro Asp Gly Gly
            260                 265                 270

Gly Gly Gly Ala Val Asp Glu Glu His Asp Met Val Asp Val Leu Leu
        275                 280                 285
```

-continued

```
Arg Ile Gln Lys Gln Gly Asp Met Arg Val Ser Leu Asn His Gly Val
290                 295                 300
Ile Arg Ala Ala Leu Ile Asp Ala Val Gly Ala Ala Leu Asp Thr Thr
305                 310                 315                 320
Ser Thr Thr Leu Arg Trp Ala Met Ala Glu Leu Ile Ala Asn Pro Arg
                325                 330                 335
Val Met His Lys Ala Gln Leu Glu Ile Arg Arg Val Met Ala Ala Gly
                340                 345                 350
Gln Gln Arg Arg Val His Glu Ala Thr Leu Arg Asp Leu His Tyr Leu
            355                 360                 365
Lys Ala Val Ile Lys Glu Thr Leu Arg Leu His Pro Pro Ala Pro Phe
370                 375                 380
Val Pro Arg Val Cys Leu Asp Asp Gly Ile Lys Ile Gln Gly Tyr His
385                 390                 395                 400
Val Pro Arg Gly Thr Ile Val Val Ala Asn Val Trp Ala Ile Ser Arg
                405                 410                 415
Asp Pro Lys Tyr Trp Glu Asp Pro Asp Met Phe Ile Pro Glu Arg Phe
                420                 425                 430
His Gln Gly Asp Pro Asp His His Arg Cys Phe Asp Phe Lys Gly Phe
            435                 440                 445
Asp Phe Glu Phe Thr Pro Phe Gly Ala Gly Arg Arg Met Cys Pro Gly
450                 455                 460
Met Asn Phe Ala His Met Asn Val Glu Ile Ala Leu Ala Ser Leu Leu
465                 470                 475                 480
Tyr His Phe Asp Trp Lys Leu Pro Asp Gly Ala Thr Pro Glu Glu Ile
                485                 490                 495
Asp Met Thr Glu Leu Trp Gly Val Thr Val Ala Arg Lys Ala Lys Leu
                500                 505                 510
Leu Leu His Pro Ile Pro Cys Ile Pro Ala Ala Ala Ser Ile Asp Ala
            515                 520                 525

<210> SEQ ID NO 13
<211> LENGTH: 1902
<212> TYPE: DNA
<213> ORGANISM: Sorghum bicolor

<400> SEQUENCE: 13
acacacagca gcagctcaat cgtgctagct agctgcgagc aggtgtacac gtacacacac      60
aattaagtca ccaacaatgg aagtgttcca acccctcctc gtcgtctccg ccattgccgt     120
ggccctagtg cacctcctca ggcacctgat ggtgaggcct actagcagca ggcacccgcc     180
ggggccgtgg aagcttccgg tgatcggcag catgcaccac ctggtgaacg tgctcccgca     240
ccgcgcgctc cgggacctcg ccggcgtcca cggcccgctc atgatgctgc agctgggcga     300
gaccccgctg gtggtcgcgt cgtccaggga gatggcgcgc aggtgctca gacgcacga     360 cgccaacttc gccacccgcc caagctcct cagcggcgag atcgtcctct accgctgggc     420
cgacatcctc ttctcgctgt ccggcgagta ctggcgcaag ctccgccagc tctgcgccgc     480
cgaggtcctc agcccaaaac gtgtcctcac cttccgacac atcagggaac aggagatggc     540
gagtcatgtg gaaaggatac gagcagccgg gccatcgacg gccgtggacc tcagcgagac     600
attctacaac ctggcgatca gcatcgtctc ccgcgcatcc ttcggcaaca gcagaggaa     660 cgccggcggg ttcctgacgg cgatgaaagc cggcgtcgcg ctgtccagcg gcttcaagct     720
ccccgacctc ttccccacct ggcggcccgt gctcgccgcg gtgaccggca tgcggcgcac     780
```

-continued

```
gctggaggac atccacagga cggtggactc caccctggag gaggtcatag aggagaggac    840
gcgtgcccgg gacgagaagc tgcaggcaac gataaggtca tcgttgtctg gccgaagccc    900
aacagacacc gccgccgccg ccgacgacga cgacgagaac ctcgtcgacc tcctcatcgg    960
cctgcaggag cgagcttctt cttcctcagg gtcgtcgtcg ttccacctca accggaacag   1020
catcaaggcg atcatattcg acatgttcac cgccgggacg ggcacgctgg cgtcgtcgct   1080 ggactgggc atgtcggagc tgatgaggaa ccagagggtg atgggcaagc tgcagcgcga   1140
ggtccgggag gcgttccggg acaggcggc cgtctcggag gccgacatcc aggcggccga   1200
cctgccgtac ctgaagctcg tgatcaagga cgctccggg ctgcacccgc cggtgccgct   1260
gctggtgccg cgggagagca tcgacgagtg cgagatcgag ggctacacga ttccggcgag   1320
gtcccgggtg atcgtcaacg cgtgggctgt cggaagagac cccaagtact gggaggacgc   1380
cgacgagttc aagcccgaga ggttcgacgg cgacgtcgct gctgatttca tgggggtag   1440 ctacgagtac ataccgttcg gtgctggacg gaggatgtgc ccggggattt cctatgggct   1500
gccggtcttg gagatggcga tcgtgcagct cctctaccac tttgattggt ccctgcagga   1560
gggtgtcgat gaggttgaca tgacagaggc acctggcctt ggtgtccgcc gcaagtcgcc   1620
tctgatgctc tgtgctaccc cggtcgtttc cgcgaaacc agcagggtgc caagctagaa   1680
attaactgta taggttggtt aaaatgtgtc ttccactatt tttagtacat cacatagcca   1740
ccgccatgtt aactagtagt actatgactc acgatatata tatgcgagaa agagaataac   1800
aaacacatgt atatatttca tgttagaatg atttcagata acactcacac caactagtac   1860
aagtaataaa ttgttacttt tcttaaaaaa aaaaaaaaaa aa                       1902
```

<210> SEQ ID NO 14
<211> LENGTH: 533
<212> TYPE: PRT
<213> ORGANISM: Sorghum bicolor

<400> SEQUENCE: 14

```
Met Glu Val Phe Gln Pro Leu Leu Val Val Ser Ala Ile Ala Val Ala
1               5                  10                  15

Leu Val His Leu Leu Arg His Leu Met Val Arg Pro Thr Ser Ser Arg
            20                  25                  30

His Pro Pro Gly Pro Trp Lys Leu Pro Val Ile Gly Ser Met His His
        35                  40                  45

Leu Val Asn Val Leu Pro His Arg Ala Leu Arg Asp Leu Ala Gly Val
    50                  55                  60

His Gly Pro Leu Met Met Leu Gln Leu Gly Glu Thr Pro Leu Val Val
65                  70                  75                  80

Ala Ser Ser Arg Glu Met Ala Arg Gln Val Leu Lys Thr His Asp Ala
                85                  90                  95

Asn Phe Ala Thr Arg Pro Lys Leu Leu Ser Gly Glu Ile Val Leu Tyr
            100                 105                 110

Arg Trp Ala Asp Ile Leu Phe Ser Leu Ser Gly Glu Tyr Trp Arg Lys
        115                 120                 125

Leu Arg Gln Leu Cys Ala Ala Glu Val Leu Ser Pro Lys Arg Val Leu
    130                 135                 140

Thr Phe Arg His Ile Arg Glu Gln Glu Met Ala Ser His Val Glu Arg
145                 150                 155                 160

Ile Arg Ala Ala Gly Pro Ser Thr Ala Val Asp Leu Ser Glu Thr Phe
                165                 170                 175
```

-continued

```
Tyr Asn Leu Ala Ile Ser Ile Val Ser Arg Ala Ser Phe Gly Asn Lys
                180                 185                 190

Gln Arg Asn Ala Gly Gly Phe Leu Thr Ala Met Lys Ala Gly Val Ala
            195                 200                 205

Leu Ser Ser Gly Phe Lys Leu Pro Asp Leu Phe Pro Thr Trp Arg Pro
        210                 215                 220

Val Leu Ala Ala Val Thr Gly Met Arg Arg Thr Leu Glu Asp Ile His
225                 230                 235                 240

Arg Thr Val Asp Ser Thr Leu Glu Glu Val Ile Glu Arg Thr Arg
                245                 250                 255

Ala Arg Asp Glu Lys Leu Gln Ala Thr Ile Arg Ser Ser Leu Ser Gly
            260                 265                 270

Arg Ser Pro Thr Asp Thr Ala Ala Ala Asp Asp Asp Glu Asn
        275                 280                 285

Leu Val Asp Leu Leu Ile Gly Leu Gln Glu Arg Ala Ser Ser Ser Ser
        290                 295                 300

Gly Ser Ser Ser Phe His Leu Asn Arg Asn Ser Ile Lys Ala Ile Ile
305                 310                 315                 320

Phe Asp Met Phe Thr Ala Gly Thr Gly Thr Leu Ala Ser Ser Leu Asp
                325                 330                 335

Trp Gly Met Ser Glu Leu Met Arg Asn Gln Arg Val Met Gly Lys Leu
                340                 345                 350

Gln Arg Glu Val Arg Glu Ala Phe Arg Gly Gln Ala Ala Val Ser Glu
            355                 360                 365

Ala Asp Ile Gln Ala Ala Asp Leu Pro Tyr Leu Lys Leu Val Ile Lys
370                 375                 380

Glu Thr Leu Arg Leu His Pro Pro Val Pro Leu Leu Val Pro Arg Glu
385                 390                 395                 400

Ser Ile Asp Glu Cys Glu Ile Glu Gly Tyr Thr Ile Pro Ala Arg Ser
                405                 410                 415

Arg Val Ile Val Asn Ala Trp Ala Val Gly Arg Asp Pro Lys Tyr Trp
            420                 425                 430

Glu Asp Ala Asp Glu Phe Lys Pro Glu Arg Phe Asp Gly Asp Val Ala
        435                 440                 445

Ala Asp Phe Met Gly Gly Ser Tyr Glu Tyr Ile Pro Phe Gly Ala Gly
450                 455                 460

Arg Arg Met Cys Pro Gly Ile Ser Tyr Gly Leu Pro Val Leu Glu Met
465                 470                 475                 480

Ala Ile Val Gln Leu Leu Tyr His Phe Asp Trp Ser Leu Gln Glu Gly
                485                 490                 495

Val Asp Glu Val Asp Met Thr Glu Ala Pro Gly Leu Gly Val Arg Arg
            500                 505                 510

Lys Ser Pro Leu Met Leu Cys Ala Thr Pro Val Val Ser Arg Glu Thr
        515                 520                 525

Ser Arg Val Pro Ser
        530

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
```

```
<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
ttatgcatca atcgatgcag cagctg                                    26

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
taccatggaa gtgttccaac ccctcc                                    26

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctagcttggc accctgctgg tttc                                      24
```

(preceding line: taccatggac gaatactttg ttgacctgc    29)

We, the inventors, claim:

1. An expression vector comprising a promoter and a heterologous polynucleotide; wherein said heterologous polynucleotide encodes a protein having the amino acid sequence of SEQ ID NO: 12; wherein said promoter is operatively linked to said heterologous polynucleotide, wherein said promoter is selected from the group consisting of constitutive promoter and inducible promoter, and wherein said protein has pentadecatrienyl resorcinol hydroxylase activity.

2. An expression cassette comprising a promoter and a heterologous polynucleotide, wherein said heterologous polynucleotide encodes a protein having the amino acid sequence of SEQ ID NO: 12, wherein said promoter is operably linked to said heterologous polynucleotide, and wherein said protein has pentadecatrienyl resorcinol hydroxylase activity.

3. A transformed cell capable of producing pentadecatrienyl resorcinol hydroxylase, said transformed cell comprising the expression cassette of claim 2, wherein the transformed cell is selected from the group consisting of a plant cell, a fungal cell, a blue-green algal cell, and a bacterial cell.

4. A transgenic organism capable of producing pentadecatrienyl resorcinol hydroxylase, said transgenic organism comprising the transformed cell of claim 3, wherein said transgenic organism produces elevated levels of pentadecatrienyl resorcinol hydroxylase compared to the levels of pentadecatrienyl resorcinol hydroxylase produced by the non-transformed organism, wherein the transgenic organism is selected from the group consisting of a plant, a fungus, a blue-green alga, and a bacterium.

5. An expression vector comprising a promoter and a heterologous polynucleotide wherein said polynucleotide comprises the DNA sequence of SEQ ID NO:11, wherein said polynucleotide is operably linked to said promoter, and wherein said polynucleotide encodes a pentadecatrienyl resorcinol hydroxylase.

6. An expression cassette comprising a promoter and a polynucleotide comprising SEQ ID NO: 11, wherein said promoter is operably linked to said polynucleotide, and wherein said polynucleotide encodes a protein having pentadecatrienyl resorcinol hydroxylase activity.

7. A transformed cell capable of producing pentadecatrienyl resorcinol hydroxylase, said transformed cell comprising the expression cassette of claim 6, wherein the transformed cell is selected from the group consisting of a plant cell, a fungal cell, a blue-green algal cell, and a bacterial cell.

8. A transgenic organism capable of producing pentadecatrienyl resorcinol hydroxylase, said transgenic organism the transformed cell of claim 7, wherein said transgenic organism produces elevated levels of pentadecatrienyl resorcinol hydroxylase compared to the levels of pentadecatrienyl resorcinol hydroxylase produced by the non-transformed organism, and wherein the transgenic organism is selected from the group consisting of a plant, a fungus, a blue-green alga, and a bacterium.

9. A transformed cell that has elevated levels of pentadecatrienyl resorcinol hydroxylase compared to the level of pentadecatrienyl resorcinol hydroxylase present in the untransformed cell, said transformed cell comprises an expression vector wherein said expression vector comprises heterologous DNA encoding said pentadecatrienyl resorcinol hydroxylase and a promoter, wherein said promoter is operably linked to said heterologous DNA, wherein said pentadecatrienyl resorcinol hydroxylase has the amino acid sequence of SEQ ID NO:12, and wherein said transgenic organism is selected from the group consisting of a plant, a fungus, a blue-green alga, and a bacterium.

10. A method of manipulating pentadecatrienyl resorcinol hydroxylase levels in a transformed cell or a transformed organism, said method comprising introducing into a wild-type cell or a wild-type organism an expression vector comprising a heterologous polynucleotide and a promoter to produce said transformed cell or said transformed organism, wherein said polynucleotide is operably linked to said promoter, wherein said promoter is active in said cell or organism, wherein said polynucleotide encodes a polypeptide having the amino acid sequence of SEQ ID NO:12, wherein said polypeptide has pentadecatrienyl resorcinol hydroxylase activity, wherein said cell or organism are selected from the group consisting of a plant, a fungus, a blue-green alga, and a bacterium; and allowing the production of pentadecatrienyl resorcinol hydroxylase in said transformed cell or transformed organism.

11. A transformed plant cell or plant made by the method of claim 10, or progeny thereof, wherein said transformed plant cell or plant or progeny thereof is selected for having increased levels of pentadecatrienyl resorcinol hydroxylase as compared to the level of pentadecatrienyl resorcinol hydroxylase present in the non-transformed plant cell or plant of the same variety.

12. The expression cassette of claim 2 wherein said promoter is an inducible promoter.

13. The expression cassette of claim 2 wherein said promoter is a constitutive promoter.

14. The expression cassette of claim 2 wherein said promoter is a tissue-specific promoter.

15. The expression cassette of claim 6 wherein said promoter is an inducible promoter.

16. The expression cassette of claim 6 wherein said promoter is a constitutive promoter.

17. The expression cassette of claim 6 wherein said promoter is a tissue-specific promoter.

* * * * *